(12) United States Patent
Shankar et al.

(10) Patent No.: US 8,772,471 B2
(45) Date of Patent: Jul. 8, 2014

(54) TARGETED DELIVERY OF SIRNA

(75) Inventors: Premlata Shankar, El Paso, TX (US); Sang-Kyung Lee, Seoul (KR); Manjunath Narasimhaswamy, El Paso, TX (US); Priti Kumar, Hamden, CT (US); Haoquan Wu, Jamaica Plain, MA (US); Hong-Seok Ban, Seoul (KR)

(73) Assignees: Industry-University Cooperation Foundation Hanyang University, Seoul (KR); Immune Disease Institute, Boston, MA (US)

( * ) Notice: Subject to any disclaimer, the term of this patent is extended or adjusted under 35 U.S.C. 154(b) by 282 days.

(21) Appl. No.: 12/524,536

(22) PCT Filed: Jan. 25, 2008

(86) PCT No.: PCT/US2008/052054
§ 371 (c)(1),
(2), (4) Date: Apr. 14, 2010

(87) PCT Pub. No.: WO2008/092081
PCT Pub. Date: Jul. 31, 2008

(65) Prior Publication Data
US 2010/0209440 A1    Aug. 19, 2010

Related U.S. Application Data

(60) Provisional application No. 60/897,720, filed on Jan. 26, 2007.

(51) Int. Cl.
*C07H 21/04* (2006.01)
*C12N 15/11* (2006.01)

(52) U.S. Cl.
USPC .................................... 536/24.5; 514/44 A

(58) Field of Classification Search
USPC ..................................... 536/24.5; 514/44 A
See application file for complete search history.

(56) References Cited

U.S. PATENT DOCUMENTS 7,740,880 B2 *    6/2010    Kim et al. .................... 424/450

FOREIGN PATENT DOCUMENTS

WO    WO 02069930 A1 *    9/2002
WO    2007/127219 A2    11/2007

OTHER PUBLICATIONS

Li et al. (Cancer Gene Therapy, 2001; vol. 8, pp. 555-565).*
Song E et al., "Antibody mediated in vivo delivery of small interfering RNAs via cell-surface receptors." Nat Biotechnol 23(6):709-717, 2005.
Vornlocher HP., "Antibody-directed cell-type-specific delivery of siRNA." Trends Mol Med. 12(1):1-3, 2006.
Bremer E. et al., "Target cell-restricted apoptosis induction of acute leukemic T cells by a recombinant tumor necrosis factor-related apoptosis-inducing ligand fusion protein with specificity for human CD7." Cancer Res. 65 (8):3380-3388, 2005.
Kumar P. et al., "T cell-specific siRNA delivery suppresses HIV-1 infection in humanized mice." Cell. 134(4):577-586, 2008.
Kumar P. et al., "Transvascular delivery of small interfering RNA to the central nervous system." Nature. 448 (7149):39-43, 2007.

* cited by examiner

*Primary Examiner* — J. E. Angell
(74) *Attorney, Agent, or Firm* — Nixon Peabody LLC.

(57) ABSTRACT

The present invention provides a method of delivering RNA interference molecules to a cell or a cell in a subject, which comprises contacting the cell with a protein-double stranded RNA complex, the complex comprising the double stranded RNA segment containing a double stranded RNA of interest and a protein, the protein comprising (1) a targeting moiety, which will specifically bind to a site on a target cell, and (2) a binding moiety linked thereto, which will bind to the double stranded RNA, wherein the double stranded RNA segment is delivered to a cell and effects RNA interference of the target RNA in the cell.

6 Claims, 22 Drawing Sheets

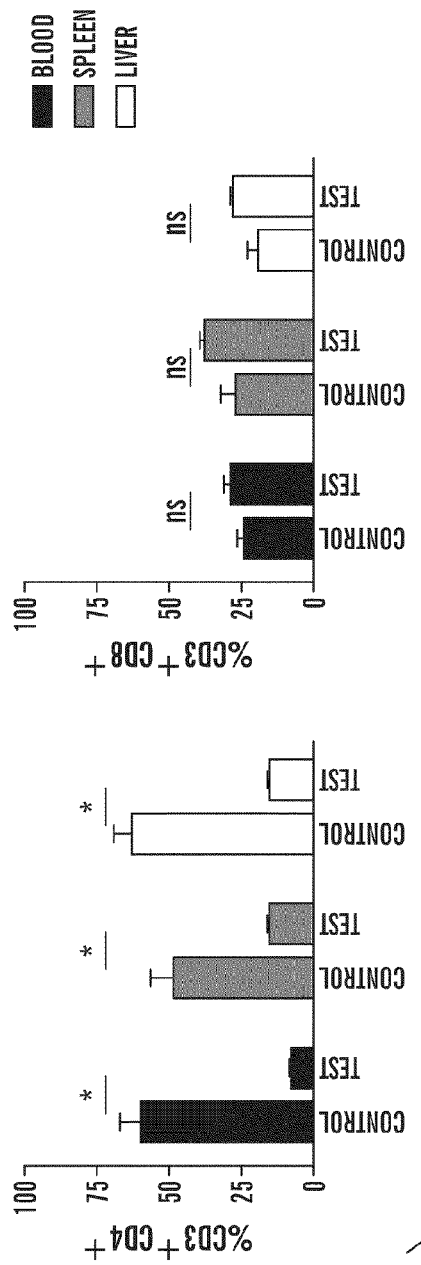
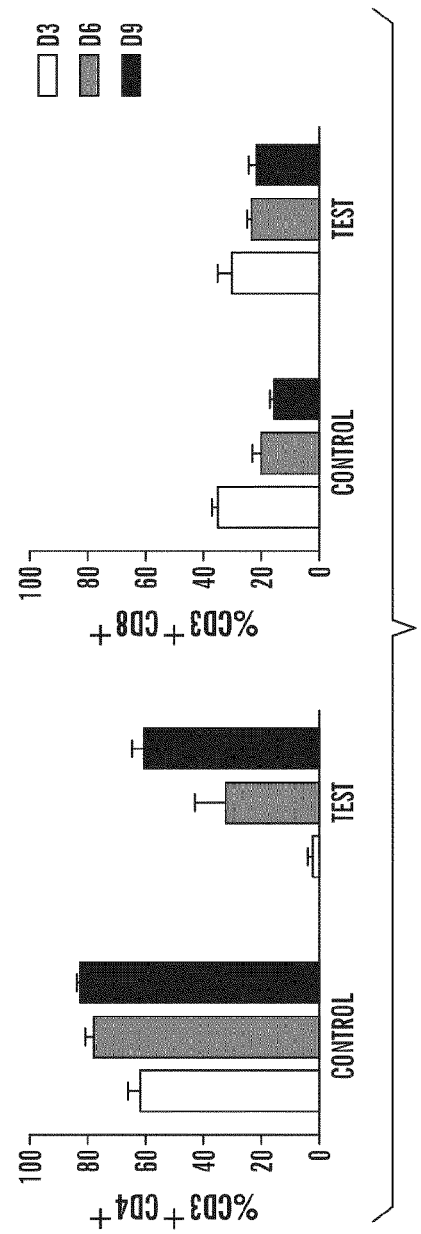
FIG. 1D
FIG. 1E

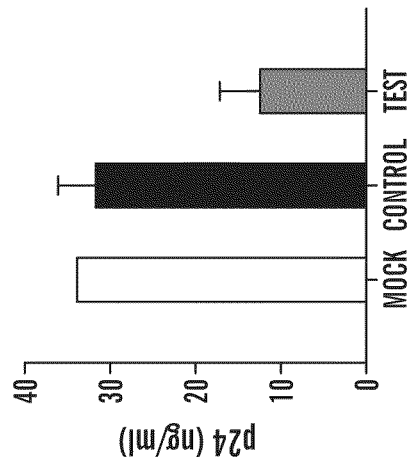
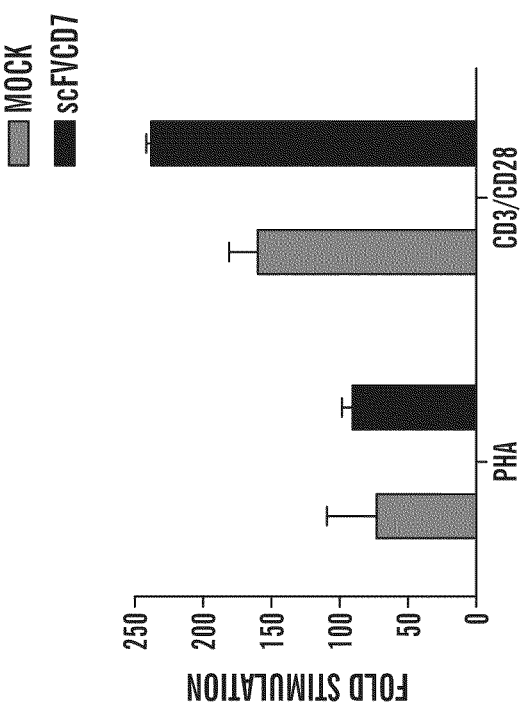

```
                         SEQUENCE LISTING

<160> NUMBER OF SEQ ID NOS: 7

<210> SEQ ID NO 1
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gcggccgcac gcagccagag ccggagcaga tattaccgcc agagacaaag aagtcgcaga      60
cgaaggaggc ggagctgcca gacacggagg agagccatga gatctcatca tcaccaccac    120
cattaa                                                               126

<210> SEQ ID NO 2
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gcggccgcaa tggccaggta cagatgctgt cgcagccaga gccggagcag atattaccgc      60
cagagacaaa gaagtcgcag acgaaggagg cggagctgcc agacacggag gagagccatg    120
agatctcatc atcaccacca ccattaa                                        147

<210> SEQ ID NO 3
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
gcggccgcac gcagccagag ccggagcaga tattaccgcc agagacaaag aagtcgcaga    60
cgaaggaggc ggagctgcca gacacggagg agagccatga ggtgttgtcg ccccaggtac   120
agaccgagat gtagaagaca cagatctcat catcaccacc accattaa                168

<210> SEQ ID NO 4
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gcggccgcac gcagccagag ccggagcaga tattaccgcc agagacaaag aagtcgcaga    60
cgaaggaggc ggagcagatc tcatcatcac caccaccatt aa                     102

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcggccgccg gcggaggagg atctcatcat caccaccatt aa                      42

<210> SEQ ID NO 6
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gcggccgcaa tggccaggta cagatgctgt cgcagccaga gccggagcag atattaccgc    60
cagagacaaa gaagtcgcag acgaaggagg cggagcagat ctcatcatca ccaccaccat   120
taa                                                                123

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Cys
1               5
```

TARGETED DELIVERY OF SIRNA

CROSS REFERENCE TO RELATED APPLICATIONS

This application is a 371 National Phase Entry Application of co-pending International Application PCT/US2008/052054 filed Jan. 25, 2008, which designated the U.S., and claims the benefit under 35 U.S.C. §119(e) of U.S. Provisional Application Ser. No. 60/897,720 filed Jan. 26, 2007, the contents of which are incorporated herein by reference.

GOVERNMENT SUPPORT

This invention was made with U.S. Government Support under AI071882 and AI0754419 awarded by the National Institutes of Health and National Institute of Allergy and Infectious Diseases (NIAID) and the U.S. Government has certain rights in this invention. This invention was also made with Korea Government support under R01-2006-000-10506-0 and F104AA010005-07A0101-00510 awarded by the Korea Ministry of Science and Technology.

FIELD OF THE INVENTION

The present invention is directed to methods of RNA interference, particularly the delivery of small interfering RNAs (siRNAs) into target cells expressing CD7.

BACKGROUND OF THE INVENTION

Much attention has been paid recently to RNA interference (RNAi), a technique in which exogenous, double-stranded RNAs (dsRNAs) are introduced into a cell to specifically destroy a particular mRNA or block its expression, thereby diminishing or abolishing gene expression (A. Fire et al., "Potent and specific genetic interference by double-stranded RNA in *Caenorhabditis elegans*," *Nature*, 391:806-11, 1998). Specific types of RNAs, such as small interfering RNAs (siRNAs) and micro interfering RNAs (miRNAs) have been shown to inhibit expression of a number of specific genes effectively and the technique has proven effective in *Drosophila, Caenorhabditis elegans*, plants, and recently, in mammalian cell cultures (S. M. Elbashir et al., "Duplexes of 21-nucleotide RNAs mediate RNA interference in cultured mammalian cells," *Nature*, 411:494-8, 2001). Because small interfering RNA molecules are directed to a specific target and thereby silence a specific gene, they have been suggested to be useful in treatment of diseases as well as for screening new pharmaceuticals and disease mechanisms for pharmaceutical target determination. However, while a number of applications, both therapeutic and screening methods, have been suggested, delivery of RNA interfering agents, including siRNAs and miRNAs, into cells has proven to be the bottleneck.

Currently known methods to deliver RNA interference into cells include chemical transfection using lipid-based, amine-based and polymer-based techniques, and combinations thereof (see, for example, products from Ambion Inc., Austin, Tex.; and Novagen, EMD Biosciences, Inc, an Affiliate of Merck KGaA, Darmstadt, Germany). Unfortunately, efficient transfer of RNA interfering agents, including siRNAs into primary cells by chemical transfection seems to be restricted to a few cell types (Ovcharenko D (2003) "Efficient delivery of siRNAs to human primary cells." Ambion TechNotes 10 (5): 15-16).

Other described ways to deliver siRNAs include expressing short hairpin RNA molecules from vectors, such as lentiviral constructs, and introducing siRNA molecules into cells using electroporation. However, feline FIV lentivirus vectors which are based on the feline immunodeficiency virus (FIV) retrovirus and the HIV lentivirus vector system, which is base on the human immunodeficiency virus (HIV), carry with them problems related to permanent integration. Electroporation is often a relatively harsh treatment and cannot generally be used to deliver siRNAs into cells in vivo.

An additional problem with all the traditional gene delivery methods discussed above for the use of delivering RNA interference is that they target all cells non-specifically. Therefore, it would be useful to develop gene delivery methods that could be targeted to specific cells thereby minimizing or avoiding potential side effects caused by delivery of RNA interference into non-target cells. Additionally, effective interference RNA delivery methods that could avoid viral vectors and could be used for both in vivo and in vitro delivery of RNA interference, including siRNA, would be desirable.

Moreover, several cell types have proven extremely difficult to transduce with siRNAs using traditional vectors, including viral vectors, liposomes and the like. Such cell types include immune system cells such as lymphocytes and dendritic cells, and stem cells.

One such cell type is T cells. Accordingly, the evaluation of the therapeutic potential of siRNA for HIV infection has been hampered by the challenges of delivery to T cells and till recently, the lack of an effective small animal model. The toxicity and frequent treatment failures associated with HAART has focused attention on the potent gene silencing mechanism of RNAi as an alternate treatment strategy for HIV infection[1-4]. Several in vitro studies have shown the potential of RNAi for effective suppression of HIV infection in cell lines and primary human T cells and macrophages, the prime targets of HIV[5-9]. However for actual therapeutic use, many parameters such as effective siRNA delivery to susceptible cells, antiviral efficacy and toxicity need to be tested in vivo. The recently described IL2 receptor common gamma chain null (IL2r$\gamma^{-/-}$) strains of immunodeficient mice allow efficient reconstitution of human immune cells making them amenable for HIV infection[10-13], but siRNA delivery to primary human T cells still remains a hurdle. Thus, so far no study has actually tested the potential of siRNA treatment to suppress HIV infection in vivo.

Therefore, to utilize fully the potential in treatment and drug screening of the discovered RNA interference, including siRNAs, it is necessary to develop ways to deliver siRNAs into cells both in vitro and in vivo.

SUMMARY OF THE INVENTION

The present invention relates to a method to deliver an RNA interference molecule to a cell or a cell present in a subject. In one embodiment, the present invention relates to an RNAi-complex, such as a siRNA-complex or miRNA-complex which comprises a target moiety, such as an antibody or antigen binding fragment thereof which targets cell surface antigen, for example a T-cell cell-surface antigen which is internalized when the targeting moiety binds, such as a CD7 receptor present on T-cells, where the targeting moiety is associated with a binding moiety, such as a protein such as a protamine fragment or homologue thereof, or nucleic acid binding domain of a protein, and where the binding moiety is associated with the RNA interference molecule, such as an siRNA or miRNA.

The methods and compositions as disclosed herein are useful in the delivery of RNAi molecules to a cell. In some embodiments, the methods and compositions as disclosed herein are useful for the treatment and/or prevention (prophylactic treatment) of diseases and disorders, for example, the treatment and/or prevention of T cell related diseases and disorders, for example for the treatment and/or prevention of a disease or disorder in a subject where the subject has T-cell deficiency or reduced level of T cells as compared to a normal healthy subject. In alternative embodiments, the methods and compositions are useful for the treatment and/or prevention of a disease or disorder in a subject where the subject has increased T-cell proliferation and/or increased T cell levels as compared to a normal healthy subject. In some embodiments, the methods and compositions as disclosed herein are useful for the prevention of HIV infection or treatment of subjects infected with HIV. In alternative embodiments, the methods and compositions as disclosed herein are useful for the prevention and/or treatment of cancers, for example but not limited to T-cell lymphoma and the like.

One aspect of the present invention relates to a method of delivering an RNA interference inducing molecule to a cell, the method comprising contacting the cell with a fusion protein-double stranded RNA complex, the complex comprising: (a) an RNA molecule comprising a double stranded RNA segment, wherein one of the strands is complementary and the other strand identical to an RNA interference target RNA; and (b) a protein, comprising (1) a targeting moiety, which specifically binds to a cell-surface antigen on a target cell, wherein the cell surface antigen internalizes when the targeting moiety binds the cell surface antigen, and (2) a binding moiety, which binds to double stranded RNA segment, wherein the double stranded RNA segment is delivered to said cell and effects RNA interference of the target gene in the cell.

Another aspect of the present invention relates to a method of delivering an RNA interference inducing molecule into a cell, the method comprising contacting the cell with a RNAi-complex consisting essentially of a targeting moiety associated with a binding moiety, and a double stranded RNA segment associated with the binding moiety, wherein (a) the double stranded RNA segment comprises one RNA strand that is complementary and the other strand identical to an RNA interference target RNA; and (b) the targeting moiety specifically binds to a cell surface antigen on a target cell, and; (c) the binding moiety binds to the double stranded RNA segment, wherein the double stranded RNA segment is delivered into said cell and effects RNA interference of the target gene in the cell.

In some embodiments, the cell surface antigen is a T-cell cell surface antigen, for example but not limited to a CD7 receptor or a homologue thereof.

In some embodiments, the double stranded RNA is an siRNA.

In some embodiments, the targeting moiety is an antibody or an antigen binding fragment thereof, for example but not limited to, a single chain antibody, a Fab portion of an antibody or a (Fab')$_2$ segment which binds to the antigen. In alternative embodiments, the binding moiety is a protein or the nucleic acid binding domain of a protein, and in some embodiments, the binding moiety is associated with the targeting moiety. In some embodiments, the targeting moiety and binding moiety are associated by a peptide bond, for instance the targeting moiety and binding moiety are comprised as a fusion protein, wherein the binding moiety is fused to the carboxy portion of the targeting moiety.

Examples of binding moieties which are nucleic acid binding domains of a protein are, for example, but not limited to nucleic acid binding domains present in proteins selected from the group consisting of GCN4, Fos, Jun, TFIIS, FMRI, yeast protein HX, Vigillin, Mer1, bacterial polynucleotide phosphorylase, ribosomal protein S3, and heat shock protein, or a nucleic acid binding variant of any of these. In alternative embodiments, the binding moiety is a protamine or a nucleic acid binding fragment thereof, for example the binding moiety can be an RNA interference-inducing molecule-binding fragment of protamine.

In some embodiments, the double stranded RNA segment targets gene silencing of mRNA encoding c-myc, VEGF, CD4, CCR5, gag, MDM2, Apex, Ku70, or ErbB2 or homologues thereof. In alternative embodiments, the double stranded RNA segment targets gene silencing of mRNA encoding oncogenes or proto-oncogenes. In alternative embodiments, the double stranded RNA segment targets gene silencing of mRNA encoding viral genes, for example but not limited to, gene silencing of HIV genes such as tat or vif genes.

In some embodiments, the methods to deliver RNAi molecules is delivery to a cell, and in some embodiments, the cell is a cultured cell. In alternative embodiments, the cell is part of an organ or part of (i.e. present in) a subject animal or human. In some embodiments, the cell is an embryonic stem cell.

Another aspect of the present invention relates to a composition comprising a targeting moiety associated with a binding moiety, wherein a double stranded RNA segment is associated with the binding moiety, wherein the targeting moiety is an antibody or antigen binding fragment thereof, and the binding moiety is a protamine or nucleic acid binding fragment thereof or a nucleic acid binding domain of a protein.

Alternative embodiments relate to a composition consisting essentially of a targeting moiety associated with a binding moiety, and a double stranded RNA segment, wherein the targeting moiety is an antibody or an antigen binding fragment thereof, and the binding moiety is a protamine or nucleic acid binding fragment thereof or a nucleic acid binding domain of a protein.

In alternative embodiments, the composition consists of a targeting moiety associated with a binding moiety, and a double stranded RNA segment, wherein the targeting moiety is an antibody or an antigen binding fragment thereof, and the binding moiety is a protamine or nucleic acid binding fragment thereof or a nucleic acid binding domain of a protein.

In some embodiments, the composition comprises a targeting moiety which specifically binds to a cell-surface antigen on a target cell, wherein the cell surface antigen internalizes when the targeting moiety binds the cell surface antigen. In some embodiments, the target cell is a T-cell. In some embodiments, the cell surface antigen is CD7 or a homologue thereof.

In some embodiments, the targeting moiety of the composition is, for example but not limited to a single chain antibody, a Fab portion of an antibody or a (Fab')$_2$ segment or an antigen binding fragment thereof. In some embodiments, the binding moiety of the composition is, for example but not limited to a protein or the nucleic acid binding domain of a protein, and the binding moiety is associated with the targeting moiety. In some embodiments, the binding moiety of the composition is for example, but not limited to a nucleic acid binding domain of a protein selected from the group consisting of GCN4, Fos, Jun, TFIIS, FMRI, yeast protein HX, Vigillin, Mer1, bacterial polynucleotide phosphorylase, ribosomal protein S3, and heat shock protein, or a nucleic acid binding variant thereof. In alternative embodiments, the binding moiety of the composition is for example, a protamine or nucleic acid binding fragment thereof, for example but not limited to a RNA interference-inducing molecule-binding fragment of protamine.

In some embodiments, the targeting moiety and binding moiety of the composition are associated with each other or linked to each other by any means commonly known by persons of ordinary skill in the art, for example, the targeting moiety and binding moiety can be linked in the form of a fusion protein, for example, where the binding moiety is fused to the carboxy portion of the targeting moiety. It is encompassed that alternative arrangements of a fusion protein of the targeting moiety and binding moiety are useful in the methods and compositions of the present invention, for example where the binding moiety is fused to the N-terminal portion of the targeting moiety.

In some embodiments, the double stranded RNA segment of the composition targets gene silencing of mRNA encoding c-myc, VEGF, CD4, CCR5, gag, MDM2, Apex, Ku70, or ErbB2 or homologues of these. In some embodiments, the double stranded RNA segment of the composition targets gene silencing of mRNA encoding oncogenes or proto-oncogenes. In alternative embodiments, the double stranded RNA segment of the composition targets gene silencing of mRNA encoding viral genes, for example but not limited to, gene silencing of HIV genes such as tat or vif genes.

In some embodiments, the composition delivers RNAi molecules to a cell, and in some embodiments, the cell is a cultured cell. In alternative embodiments, the cell is part of an organ or part of (i.e. present in) a subject animal or human. In some embodiments, the cell is an embryonic stem cell.

Another aspect of the present invention relates to a method of delivering an RNA interference molecule to a cell in a subject, the method comprising administering a composition as disclosed herein to the subject. In some embodiments, the subject is human.

DESCRIPTION OF THE DRAWINGS

FIGS. 1A-1E show scFvCD7-9R mediated siRNA uptake and gene-silencing in T cells in vitro and in vivo. FIG. 1A shows purified human CD3$^+$ T cells (upper panels), CD19$^+$ B cells and differentiated CD14$^+$ monocyte-derived macrophages (bottom panel) were treated with 200 pmol FITC-labeled siRNA alone or siRNA mixed with the indicated reagents (black histograms). Grey, filled histograms represent mock-transfected cells. FIG. 1B shows PHA activated PBMC were treated with 400 pmole anti-huCD4 siRNA complexed to scFvCD7-9R and CD4 and CD8 expression levels (black histograms) on CD3+ T cells monitored 60 h later. Grey histograms represent cells treated with scFvCD7-9R/siLuc control. FIGS. 1C and 1D show NOD/SCIDIL2r$\gamma$c$^{-/-}$ mice which were injected i.p. with healthy donor PBMC (Hu-PBL mice). After 15 days, groups of 3 mice were injected iv with 50 µg of siLuc (control) or siCD4 (test) siRNAs complexed to scFvCD7-9R twice (16 h apart) and human CD3$^+$ T cells in peripheral blood, spleen and liver analyzed for CD4 and CD8 expression 60 h later. Representative dot plots from one mouse (FIG. 1C) and cumulative data from 3 mice (FIG. 1D) are shown. Asterisks indicate significant and ns indicate no significant differences between test and control groups. P<0.05. FIG. 1E shows mice treated with siRNA as in FIG. 1C, three times and CD4 and CD8 expression in peripheral blood T cells determined on days 3, 6 and 9 after the last injection. Error bars indicate standard deviation.

FIG. 2A shows the protocol for scFvCD7-9R/siRNA administration and immunological and virological monitoring of Hu-PBL mice infected with HIV$_{BaL}$. FIGS. 2B, 2C and 2D show Hu-PBL mice which were treated iv with 50 µg siCCR5 or control siLuc 14 days after reconstitution. Two days later, the mice were intraperitoneally infected with 10,000 TCID50 of HIV$_{BaL}$ and subsequently either mock-treated (n=2) or treated with a combination of 50 µg of siCCR5/vif/tat (test, n=4) or siLuc (control, n=4) complexed to scFvCD7-9R as indicated in FIG. 1A. CD3/CD4/CD8 T cell levels were monitored by flow cytometry. Representative dot plots from one test and one control mouse are shown in FIG. 2B, and cumulative data is shown in FIG. 2C. Quadrants at each time point were drawn in comparison with corresponding isotype controls. Numbers indicated in FIG. 2B represent percentage of total CD3$^+$ T cells. Error bars indicate standard deviations. FIG. 2D shows serum p24 levels which were measured by ELISA at the indicated times after viral challenge. Horizontal lines indicate median values.

FIG. 3A shows a protocol for siRNA/scFvCD7-9R administration and immunological and virological monitoring. FIGS. 3A, 3B and 3D show mice transplanted with PBMC from HIV-seropositive donors (4 per group) were treated iv with scFvCD7-9R complexed to either 50 µg siLuc (control) or siCCR5/vif/tat (test) as indicated in FIG. 3A, and CD4 T cell levels which were monitored by flow cytometry. Representative dot plots from one mouse in each group are shown in FIG. 3B, and cumulative data from 4 mice is shown in FIG. 3C. Numbers indicated in FIG. 3B represent percentage of total CD3 T cells. Error bars represent standard deviation. FIG. 3D show viral copy numbers in plasma which were measured by the Amplicor test on day 17 after reconstitution with donor PBMC.

FIG. 4A shows peripheral blood from Hu-HSC mice which was examined for the presence of human CD4 and CD8 T cells 12 weeks after reconstitution. FIGS. 4B and 4C show Hu-HSC mice which were iv injected with siCD4 or control siLuc complexed to scFvCD7-9R twice and peripheral blood T cells tested for CD4 and CD8 expression before and 3 days after treatment. Representative dot plots from one mouse in each group are shown in FIG. 4B, and cumulative data from 3 mice are shown in FIG. 4C. Numbers indicated in FIG. 4B represent percentage of total CD3+ T cells. In FIG. 4C, reduction in surface levels was calculated as a percentage of initial expression levels before siRNA injection. FIG. 4D shows splenocytes isolated from Hu-HSC mice 1 day after treatment with scFvCD7-9R/siLuc (control) or siCCR5 (test) were PHA-stimulated and infected with HIV$_{BaL}$ at a moi of 3 and p24 antigen levels in culture supernatants assayed in triplicate by ELISA at indicated time points. Error bars indicate standard deviation.

FIGS. 5A-5F show scFvCD7 binds to CD7 and 9R conjugation allows siRNA binding and delivery to T cells in vitro without toxic effects. FIG. 5A shows purified human CD3$^+$ T cells which were stained with fluorescently labeled antibodies to CD3, CD4 and CD7 without or after treatment with scFvCD7Cys. FIG. 5B shows T cell surface expression of CD7 was assessed at different time points after preincubation with scFvCD7Cys. FIG. 5C shows 100 pmole siRNA which was incubated with scFvCD7-9R or unconjugated scFvCD7Cys control at the indicated molar ratios for 15 min and electrophoresed on 1% agarose gels. The position of the non-bound siRNA is indicated. FIG. 5D shows staurosporine or scFvCD7-9R treated PBMC which were stained with Annexin-V 24 h after culture. FIG. 5E shows PBMC treated with scFvCD7-9R/siLuc which were stimulated with PHA or antiCD3/CD28 beads for 3 days and pulsed with 3H-thymidine for 18 h. Fold stimulation was calculated by dividing the counts incorporated in the presence to that in the absence of stimulating agent. FIG. 5F shows PBMC isolated from groups of Hu-PBL mice (as described in FIG. 2) which were PHA-stimulated and infected with HIV IIIB at a moi (multiplicities of infection) of 3. Culture supernatant collected on day 10 after infection was tested for p24 antigen level in triplicates by ELISA. Error bars indicate standard deviation.

FIG. 6A shows the kinetics of human leukocyte expansion in Hu-PBL mice which were assessed by staining of mouse peripheral blood cells with human CD45 at each indicated time point (n=3). FIG. 6B shows reconstitution of human leukocyte lineages in Hu-HSC mice which was tested by flow cytometric analysis of peripheral blood cells 12 weeks after CD34$^+$ HSC transplantation. FIG. 6C shows peripheral blood cells from Hu-HSC and Hu-PBL mice were compared for expression of naïve and activated T cell markers using indicated antibodies. Percentages corresponding to either CD45$^+$ or CD3$^+$ gated populations are indicated in the left and right panels respectively.

FIG. 7A shows a schematic of the scFv fragment specific for human CD7. FIG. 7B shows a western blot of the scFv fragment specific for CD7. FIG. 7C shows a gel retardation assay of 100 pmols of siRNA binding at various concentrations to scFvCD7-9R or scFv-CD7, where 1=25 µg, 2=50 µg, 3=75 µg and 4=125 µg. FIG. 7D shows a schematic representation of scFvCD7-9R and FIG. 7E shows a schematic representation or scFv-CD7. All the siRNA is bound to scFvCD7-9R at 75 µg and 125 µg, but does not bind at the same concentrations of scFv-CD7.

FIG. 8A shows CD7 scFv and scFv-9dR blocks CD7 staining in Jurkat cells, but CD7 scFv and scFv-9dR do not block CD4 staining, as shown in FIG. 8B.

FIG. 9A shows siFITC complexed to 9R and siFITC complexed to CD7 scFv9R (right panel). FIG. 9B shows CD7 scFv/9D-mediated delivery of siRNA specifically knocks down CD4 expression in PHA activated PBMCs.

FIG. 10A shows the flow cytometry of CD4/CD3-positive cells in mice injected with a mock CD7 scFv/9R (no siRNA attached) (top row of panels) and injected CD7 scFv/9R-complexed CD4 siRNA (lower panels) in blood, spleen and liver tissues. FIG. 10B shows quantitative analysis of FIG. 10A, showing % CD3/CD4 cells in blood, spleen and liver tissues of mice injected with a mock CD7 scFv/9R (no siRNA attached) or injected CD7 scFv/9R-complexed CD4 siRNA.

FIG. 11A shows the flow cytometry of CD8/CD3-positive cells in mice injected with a mock CD7 scFv/9R (no siRNA attached) (top row of panels) and injected CD7 scFv/9R-complexed CD4 siRNA (lower panels) in blood, spleen and liver tissues. FIG. 11B shows quantitative analysis of FIG. 11A, showing % CD3/CD8 cells in blood, spleen and liver tissues of mice injected with a mock CD7 scFv/9R (no siRNA attached) or injected CD7 scFv/9R-complexed CD4 siRNA.

DESCRIPTION OF THE INVENTION

Figure 1A:
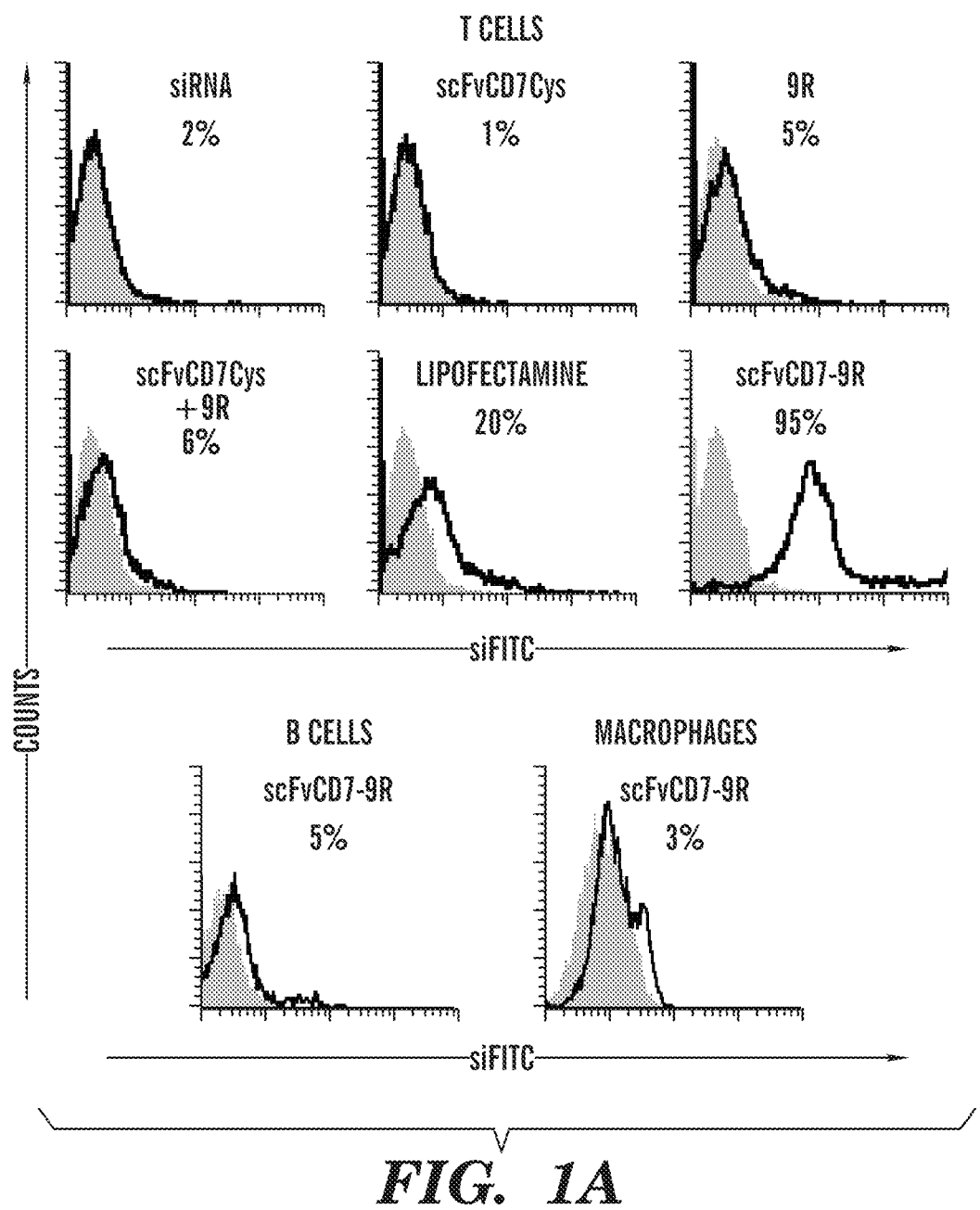

Accordingly, the present invention provides a novel method of targeted delivery both in vitro and in vivo of small interference RNAs into desired cells thus avoiding entry of the siRNA into other than intended target cells. Therefore, the method of the present invention allows treatment of specific cells with RNA interference, limiting potential side effects of RNA interference caused by non-specific targeting of RNA interference. Moreover, by specific targeting, the amount of RNA interference administered into a subject in need of treatment can be minimized because the effect of the RNA interference is concentrated into the specific target cells. Specific target cells include those expressing CD7. CD7 is a 40 kDa cell surface glycoprotein from the immunoglobulin superfamily. It is expressed on a majority of human thymocytes and a large subset (85%) of peripheral blood T cells. A key property of CD7 for therapeutic applications is its rapid internalization after binding by an antibody, even after binding by monovalent antibody fragments.

Using a novel delivery method in a humanized mouse model, the inventors show that siRNA treatment can dramatically suppress HIV infection in vivo. A single chain antibody to the pan T cell surface antigen CD7 was conjugated to an oligo-9-arginine peptide (scFvCD7-9R) for T cell-specific siRNA delivery in NOD/SCIDIL2rγ$^{-/-}$ mice reconstituted with human peripheral blood lymphocytes (Hu-PBL) or CD34$^+$ hematopoietic stem cells (Hu-HSC). T cell-specific gene-silencing was first confirmed by intravenous injection of scFvCD7-9R/CD4 siRNA complex. In HIV-infected Hu-PBL mice, treatment with a combination of siRNAs targeting cellular CCR5 and viral genes complexed to scFvCD7-9R controlled viral replication and prevented CD4 T cell loss during the 4 week period of observation. Strikingly, this approach also suppressed endogenous virus in mice reconstituted with HIV$^+$ PBMC leading to restoration of CD4 T cell counts. Moreover, scFvCD7-9R also delivered siRNAs to naïve T cells in Hu-HSC mice, rendering them resistant to HIV challenge ex-vivo. Thus, the inventors have discovered and directly demonstrated the feasibility of siRNA therapy for HIV infection in a preclinical animal model.

Accordingly, in one embodiment, the invention provides a method of RNA interference in a cell, comprising contacting the cell with a fusion protein-double stranded RNA complex, the complex comprising: an RNA molecule comprising a double stranded RNA segment, wherein one of the strands is complementary and the other strand identical to an RNA interference target RNA; and (1) a targeting moiety, which specifically binds to a site on a target cell, and (2) a binding moiety, which binds to the double stranded RNA segment, wherein the double stranded RNA segment initiates RNA interference in the cell. In one embodiment, the double stranded RNA is a siRNA. In another embodiment, the targeting moiety is an scFv.

In some embodiments, the present invention relates to a short interfering RNA (siRNA)-complex or micro interfering RNA (miRNA)-complex, which comprises a target moiety associated with a binding moiety, where the binding moiety associates with the RNA interference, such as siRNA. For example, the present invention relates to a RNAi-complex, such as a siRNA-complex or miRNA-complex which comprises a target moiety, such as an antibody or antigen-binding fragment thereof which targets T cells, where the targeting moiety is associated with a binding moiety such as a protein such as a protamine fragment or homologue thereof, or nucleic acid binding domain of a protein, or where the binding moiety associates with the RNA interference, such as siRNA or miRNA.

In particular embodiments, the siRNA-complex or miRNA-complex consists essentially of a siRNA or a miRNA, a binding moiety that binds the siRNA or miRNA and a targeting moiety.

Alternatively, in some embodiments, the siRNA-complex or miRNA-complex consists of a siRNA or a miRNA, a binding moiety that binds the siRNA or miRNA and a targeting moiety.

In some embodiments, a targeting moiety such as an antibody, or antigen-binding fragment thereof which targets T cells, binds to a cell-surface antigen on T-cells, where the T-cell cell-surface antigen is internalized (along with the bound targeting moiety and associated complex) when the targeting moiety binds to the cell-surface antigen. For example, one such cell-surface antigen present on T cells which is internalized on binding of a targeting moiety is the CD7 receptor present on T cells.

Accordingly in one embodiment, the present invention relates to an RNAi-complex, such as an siRNA-complex or miRNA-complex which comprises a target moiety, such as an antibody or antigen binding fragment thereof which targets a T-cell cell-surface antigen which is internalized when the targeting moiety binds, such as a CD7 receptor present on T-cells, where the targeting moiety is associated with a binding moiety such as a protein such as a protamine fragment or homologue thereof, or nucleic acid binding domain of a protein, where the binding moiety associates with the RNA interference, such as siRNA or miRNA.

In some embodiments, the present invention relates to an RNAi-complex, such as an siRNA-complex or miRNA-complex which consists essentially of a target moiety (such as an antibody or antigen binding fragment thereof which targets a T-cell cell-surface antigen which is internalized when the targeting moiety binds, such as a CD7 receptor present on T-cells, where the targeting moiety) associated with a binding moiety (such as a protein such as a protamine fragment or homologue thereof, or nucleic acid binding domain of a protein) associated with an RNA interference-inducing molecule, such as siRNA or miRNA.

In an alternative embodiment, the present invention relates to an RNAi-complex, such as an siRNA-complex or miRNA-complex which consists of a target moiety (such as an antibody or antigen binding fragment thereof which targets a T-cell cell-surface antigen which is internalized when the targeting moiety binds, such as a CD7 receptor present on T-cells) associated with a binding moiety (such as a protein such as a protamine fragment or homologue thereof, or nucleic acid binding domain of a protein) associated with an RNA interference-inducing molecule, such as an siRNA or miRNA.

In another embodiment, the target moiety is an antibody. In some embodiments, the antibody is a single chain antibody, a Fab portion of an antibody or a (Fab')$_2$ segment, scFv, or other antigen binding fragments of the antibody.

In one embodiment, the binding moiety is a protein or the nucleic acid binding domain of a protein. In some embodiments, the binding moiety is fused to the carboxy portion of the targeting moiety. The location of the targeting moiety may be either in the carboxyl-terminal or amino-terminal end of the construct or in the middle of the fusion protein. Alternatively, the fusion protein may comprise more than one siRNA binding moieties and one or more targeting moieties.

In another embodiment, the binding moiety is the nucleic acid binding domain of a protein selected from the group of nucleic acid binding domains present in proteins selected from the group consisting of protamine, GCN4, Fos, Jun, TFIIS, FMRI, yeast protein HX, Vigillin, Mer1, bacterial polynucleotide phosphorylase, ribosomal protein S3, and heat shock protein. In one embodiment, the binding moiety is the protein protamine or an RNA interference-inducing molecule-binding fragment of protamine. In one embodiment, the binding moiety is a peptide of nine arginines, and is referred to herein as "9R".

In one embodiment, the siRNA targets mRNA encoding c-myc, VEGF, CD4, CCR5, gag, MDM2, Apex, Ku70, or ErbB2.

In one embodiment, the cell is a cultured cell. Alternatively, the cell is part of an organ. Alternatively, the cell is part of a subject animal. In another embodiment, the cell is a stem cell, including, for example, an adult stem cell or an embryonic stem cell.

RNA Interference Inducing Molecules

In another preferred embodiment, the invention provides a method of delivering RNA interference into a cell, the method comprising contacting the cell with a fusion protein-double stranded RNA complex, the complex comprising an RNA molecule comprising a double stranded RNA segment, wherein one of the strands is complementary and the other strand identical to an RNA interference target RNA; and a targeting moiety, which specifically binds to CD7 on a target cell, and (2) a binding moiety, which binds to the double stranded RNA segment, wherein the double stranded RNA segment initiates RNA interference in the cell. Preferably, the double stranded RNA is an siRNA.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

As used herein, the term "RNA interference inducing molecule" or "RNAi molecule" or "RNAi agent" are used interchangeably herein to refer to an RNA molecule, such as a double stranded RNA, which functions to inhibit gene expression of a target gene through RNA-mediated target transcript cleavage or RNA interference. Stated another way, the RNA interference inducing molecule induces gene silencing of the target gene. The overall effect of an RNA interference inducing molecule is gene silencing of the target gene. A double-stranded RNA, such as that used in siRNA, has different properties than single-stranded RNA, double-stranded DNA or single-stranded DNA. Each of the species of nucleic acids is bound by mostly non-overlapping sets of binding proteins in the cell and degraded by mostly non-overlapping sets of nucleases. The nuclear genome of all cells is DNA-based and as such is unlikely to produce immune responses except in autoimmune disease (Pisetsky. Clin Diagn Lab Immunol. 1998 January; 51:1-6). Single-stranded RNA (ss-RNA) is the form endogenously found in eukaryotic cells as the product of DNA transcription. Cellular ssRNA molecules include messenger RNAs (and the progenitor pre-messenger RNAs), small nuclear RNAs, small nucleolar RNAs, transfer RNAs and ribosomal RNAs. Single-stranded RNA can induce interferon and inflammatory immune response via TLR7 and TLR8 receptors (Proc Natl Acad. Sci. 2004. 101: 5598-603; Science. 2004. 303:1526-9; Science. 2004. 303: 1529-3). Double-stranded RNA induces a size-dependent immune response such that dsRNA larger than 30 bp activates the interferon response, while shorter dsRNAs feed into the cell's endogenous RNA interference machinery downstream of the Dicer enzyme. MicroRNAs (miRNAs), including short temporal RNAs and small modulatory RNAs, are the only known cellular dsRNA molecules in mammals and were not discovered until 2001 (Kim. 2005. Mol Cells. 19:1-15). Response to extracellular RNA in the bloodstream, double- or single-stranded of any length, is rapid excretion by the kidneys and degradation by enzymes (PLOS Biol. 2004. 2:18-20).

As used herein, the term "effects RNA interference" refers to the initiation or causation of RNAi-mediated gene silencing, or to conditions that result in RNA interference-mediated gene silencing.

Numerous specific siRNA molecules have been designed that have been shown to inhibit gene expression (Ratcliff et al. Science 276:1558-1560, 1997; Waterhouse et al. Nature 411: 834-842, 2001). In addition, specific siRNA molecules have been shown to inhibit, for example, HIV-1 entry to a cell by targeting the host CD4 protein expression in target cells thereby reducing the entry sites for HIV-1 which targets cells expressing CD4 (Novina et al. Nature Medicine, 8:681-686, 2002). Short interfering RNA have further been designed and successfully used to silence expression of Fas to reduce Fas-mediated apoptosis in vivo (Song et al. Nature Medicine 9:347-351, 2003).

It has been shown in plants that longer, about 24-26 nt long siRNA correlates with systemic silencing and methylation of homologous DNA. Conversely, the about 21-22 nt short siRNA class correlates with mRNA degradation but not with systemic signaling or methylation (Hamilton et al. EMBO J. 2002 Sep. 2; 21(17):4671-9). These findings reveal an unexpected level of complexity in the RNA silencing pathway in plants that may also apply in animals. In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function (Herman, et al.). The use of siRNA molecules for directing methylation of a target gene is described in U.S. Provisional Application No. 60/447,013, filed Feb. 13, 2003, referred to in U.S. Patent Application Publication No. 20040091918.

It is also known that the RNA interference does not have to match perfectly to its target sequence. Preferably, however, the 5' and middle part of the antisense (guide) strand of the siRNA is perfectly complementary to the target nucleic acid sequence.

The RNA interference-inducing molecule according to the present invention includes RNA molecules that have natural or modified nucleotides, natural ribose sugars or modified sugars and natural or modified phosphate backbone.

Accordingly, the RNA interference-inducing molecule referred to in the specification includes, but is not limited to, unmodified and modified double stranded (ds) RNA molecules including, short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also may contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention have a double stranded structure. In one embodiment, the siRNA molecules of the present invention are double stranded for more than about 25%, more than about 50%, more than about 60%, more than about 70%, more than about 80%, more than about 90% of their length.

As used herein, "gene silencing" induced by RNA interference refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without introduction of RNA interference. In one preferred embodiment, the mRNA levels are decreased by at least about 70%, about 80%, about 90%, about 95%, about 99%, about 100%.

The term "reduced" or "reduce" as used herein generally means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease, or any integer decrease between 10-100% as compared to a reference level.

The term "increased" or "increase" as used herein generally means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any integer increase between 10-100% as compared to a reference level, or about a 2-fold, or about a 3-fold, or about a 4-fold, or about a 5-fold or about a 10-fold increase, or any increase between 2-fold and 10-fold or greater as compared to a reference level.

The RNA interference as described herein also includes RNA molecules having one or more non-natural nucleotides, i.e. nucleotides other than adenine "A", guanine "G", uracil "U", or cytosine "C", a modified nucleotide residue or a derivative or analog of a natural nucleotide are also useful. Any modified residue, derivative or analog may be used to the extent that it does not eliminate or substantially reduce (by at least 50%) RNAi activity of the dsRNA. These forms thus include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2'F UTP. Such modified nucleotides include, but are not limited to, aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH$_2$ uridine, 2'NH$_2$ cytidine, and 2' F uridine, including the free pho (NTP) RNA molecules as well as all other useful forms of the nucleotides.

The RNA interference as referred herein additionally includes RNA molecules which contain modifications in the ribose sugars, as well as modifications in the "phosphate backbone" of the nucleotide chain. For example, siRNA or miRNA molecules containing α-D-arabinofuranosyl structures in place of the naturally-occurring α-D-ribonucleosides found in RNA can be used in RNA interference according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly α-arabinose (U.S. Pat. No. 5,177,196 which is incorporated herein in its entirety by reference). Also, phosphorothioate linkages can be used to stabilize the siRNA and miRNA molecules (U.S. Pat. No. 5,177,196). siRNA and miRNA molecules having various "tails" covalently attached to either their 3'- or to their 5'-ends, or to both, are also been known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Various specific siRNA and miRNA molecules have been described and additional molecules can be easily designed by one skilled in the art. For example, the miRNA Database at world-wide-web address: sanger.ac.uk, followed by /Software/Rfam/mirna/index provides a useful source to identify additional miRNAs useful according to the present invention (Griffiths-Jones S. NAR, 2004, 32, Database Issue, D109-D111; Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T. RNA, 2003, 9(3), 277-279).

An "siRNA" as used herein relates to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

siRNAs also include small hairpin (also called stem loop) RNAs (shRNAs). In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In another embodiment, siRNAs useful according the methods of the present invention are found in WO 05/042719, WO 05/013886, WO 04/039957, and U.S. Pat. App. No. 20040248296 which are incorporated in their entirety herein by reference. Other useful siRNAs useful in the methods of the present invention include, but are not limited to, those found in U.S. Pat. App. Nos. 20050176666, 20050176665, 20050176664, 20050176663, 20050176025, 20050176024, 20050171040, 20050171039, 20050164970, 20050164968, 20050164967, 20050164966, 20050164224, 20050159382, 20050159381, 20050159380, 20050159379, 20050159378, 20050159376, 20050158735, 20050153916, 20050153915, 20050153914, 20050148530, 20050143333, 20050137155, 20050137153, 20050137151, 20050136436, 20050130181, 20050124569, 20050124568, 20050124567, 20050124566, 20050119212, 20050106726, 20050096284, 20050080031, 20050079610, 20050075306, 20050075304, 20050070497, 20050054598, 20050054596, 20050053583, 20050048529, 20040248174, 20050043266, 20050043257, 20050042646, 20040242518, 20040241854, 20040235775, 20040220129, 20040220128, 20040219671, 20040209832, 20040209831, 20040198682, 20040191905, 20040180357, 20040152651, 20040138163, 20040121353, 20040102389, 20040077574, 20040019001, 20040018176, 20040009946, 20040006035, 20030206887, 20030190635, 20030175950, 20030170891, 20030148507, 20030143732, and WO 05/060721, WO 05/060721, WO 05/045039, WO 05/059134, WO 05/045041, WO 05/045040, WO 05/045039, WO 05/027980, WO 05/014837, WO 05/002594, WO 04/085645, WO 04/078181, WO 04/076623, and WO 04/04635, which are all incorporated herein in their entirety by reference.

The RNA interference according to the present invention can be produced using any known techniques such as direct chemical synthesis, through processing of longer double stranded RNAs by exposure to recombinant Dicer protein or Drosophila embryo lysates, through an in vitro system derived from S2 cells, using phage RNA polymerase, RNA-dependant RNA polymerase, and DNA based vectors. Use of cell lysates or in vitro processing may further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

The RNA interference, useful in the methods of the present invention include siRNAs that target gene expression of any protein encoded inside a eukaryotic cell. Examples of these proteins include endogenous mammalian proteins, parasitic proteins, viral proteins encoded by an eukaryotic cell after entry of a virus into the cell. Examples of methods of preparing such RNA interference are shown, for example in an international patent application Nos. PCT/US03/34424, PCT/US03/34686, and U.S. provisional patent applications No. 60/488,501, 60/488,155 and 60/516,172 the contents and references of all of these patent applications are herein incorporated by reference in their entirety.

Unlike the siRNA delivery methods described in the prior art, the method of the present invention allows targeting of specific cells to minimize or to avoid completely undesired potential side effects of siRNA therapy.

Target Moiety

The target moiety specifically brings the delivery system to the target cell. The particular target moiety for delivering the interference RNAs (or RNAi), including siRNAs, can be determined empirically based upon the present disclosure and depending upon the target cell. For example, with somatic cell therapy in vivo with readily accessible cells or tissues such as an intravascular target, immune cell target or the like, the important attributes of the target moiety are affinity and selectivity.

The method of the present invention provides a system to deliver siRNA into a limited number of cells thereby limiting, for example, potential side effects of therapies using siRNA. The particular cell surface targets that are chosen for the targeting moiety will depend upon the target cell. Cells can be specifically targeted, for example, by use of antibodies against cell surface antigens such as particular proteins, lipids or carbohydrates that are present on the cell surface. A skilled artisan is easily able to determine such molecules based on the general knowledge in the art.

In some embodiments, the target moiety is an antibody. The antibody is preferably a single chain antibody, a Fab portion of an antibody or a (Fab')$_2$ segment or scFv.

The term "target cell" as used herein refers to a cell which comprises cell surface antigens, such as for example but not limited to, cell surface receptors or glycoprotein or other cell surface markers which the targeting moiety as disclosed herein can recognize and bind thereto.

The terms "targeting moiety" or "target moiety" are used interchangeably herein and refer to a molecule which has affinity, or binds to a molecule on the surface of a target cell, for example a targeting moiety functions as an agent that homes in on or preferentially associates or binds to a particular tissue, cell type, receptor, infecting agent or other area of interest. Examples of a targeting moiety include, but are not limited to, an antibody, an antigen binding fragment of an antibody, an antigen, a ligand, a receptor, one member of a specific binding pair, a polyamide including a peptide having affinity for a biological receptor, an oligosaccharide, a polysaccharide, a steroid or steroid derivative, a hormone, e.g., estradiol or histamine, a hormone-mimic, e.g., morphine, or other compound having binding specificity for a cellular target. In the methods of the present invention, a targeting moiety promotes transport or preferential localization of the RNAi molecule to a target cell, for example a T-cell target cell.

Any antibody with a known sequence can be used as a targeting moiety according to the methods as disclosed herein to prepare a construct as described above. As used herein, an "antibody" or "functional fragment" of an antibody encompasses polyclonal and monoclonal antibody preparations, as well as preparations including hybrid or chimeric antibodies, such as humanized antibodies, altered antibodies, F(ab')$_2$ fragments, F(ab) fragments, Fv fragments, single domain antibodies, dimeric and trimeric antibody fragment constructs, minibodies, and functional fragments thereof which exhibit immunological binding properties of the parent antibody molecule and/or which bind a cell surface antigen.

As described, the second portion of the protein is the binding moiety. In one embodiment, one uses a single vector containing gene segments that will express both the targeting moiety and the binding moiety. However, one can use a vector system to co-transfect a cell with at least two vectors and select for cells expressing the fusion protein. Preferably, one uses a single vector. One preferably attaches the sequence encoding the target moiety to a gene, or gene segment, encoding the binding moiety by standard means. For example, a gene for human protamine (Balhorn, J. of Cell. Biol. 93:298-305 (1982)).

If antibodies are used as a targeting moiety, the use of single chain antibodies as the target moiety is preferable. However, when the target cell is not readily accessible, such as when the cell is part of a large solid tumor mass with a poor blood supply and high interstitial pressure, the serum half-life is important to consider. In such instances, the full antibody and (Fab')$_2$ segments are typically preferred. In one embodiment, one could synthesize the fusion protein so that the binding moiety is attached to the carboxy-terminus of the light or heavy chain of an intact immunoglobulin, such as IgG$_1$.

In order to limit antigenic reaction, the targeting moiety is preferably selected to take into account the host animal whose cells will be targeted. Thus, if the target animal is a mouse, one preferably uses murine antibodies, whereas if the target animal is a human, one preferably uses a human antibody or a humanized antibody.

In one embodiment, a vector encoding siRNA is delivered into a specific target cell. As used herein, the term "vector" is used in reference to nucleic acid molecules that transfer DNA segment(s) from one cell to another. Vectors are often derived from plasmids, bacteriophages, or plant or animal viruses. The term "expression vector" as used herein refers to a recombinant DNA molecule containing a desired siRNA coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In one embodiment, one can also use localization sequences to deliver the released RNA interference-inducing molecule intracellularly to a cell compartment of interest. In one embodiment the RNAi-delivery system as disclosed herein uses this internalization system, for example the targeting moiety first binds to a specific cell surface antigen, for example a receptor on the cell. Thereafter, the targeted cell internalizes the RNAi-delivery system (which also comprises the RNAi), which is bound to the cell.

In some embodiments, the targeting moiety binds to membrane proteins on the cell surface, including receptors and antigens which can be internalized by receptor mediated endocytosis after interaction with the ligand to the receptor or antibodies. (Dautry-Varsat, A., et al., Sci. Am. 250:52-58 (1984)). This endocytic process is exploited by the delivery system as disclosed herein. Because this process can damage the RNA interference-inducing molecule as it is being internalized, in some embodiments it may be desirable to use a segment containing multiple repeats of the RNA interference-inducing molecule of interest. In some embodiments, one can also include sequences or moieties that disrupt endosomes and lysosomes. See, e.g., Cristiano, R. J., et al., Proc. Natl. Acad. Sci. USA 90:11548-11552 (1993); Wagner, E., et al., Proc. Natl. Acad. Sci. USA 89:6099-6103 (1992); Cotten, M., et al., Proc. Natl. Acad. Sci. USA 89:6094-6098 (1992).

Short interfering RNA (siRNA)-complex or micro interfering RNA (miRNA)-complex as referred to herein is a complex wherein a target moiety is associated or complexed or mixed with the RNA interference, such as siRNA. Suitable siRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DE AE-albumin and DEAE-dextran, polymethylacrylate, polyhexylacrylate, poly(D,L-lactic acid), poly(DL-lactic-co-glycolic acid (PLGA), alginate, and polyethyleneglycol (PEG), and polyethylenimine. In one embodiment, the interference RNA-binding domain is selected from the nucleic acid binding domains present in proteins selected from the group consisting of GCN4, Fos, Jun, TFIIS, FMRI, yeast protein HX, Vigillin, Mer1, bacterial polynucleotide phosphorylase, ribosomal protein S3, and heat shock protein.

Cell Surface Antigens Targets for the Targeting Moiety

In one embodiment, the present invention comprises a targeting moiety which binds to a cell-surface antigen which is internalized on binding of the targeting moiety. For example, one such cell-surface antigen is a receptor present on T cells which is internalized on binding of a targeting moiety, such as but not limited to a CD7 receptor present on T cells. Accordingly in one embodiment, the present invention relates to a RNAi-complex, such as an siRNA-complex or miRNA-complex which comprises of a target moiety, such as an antibody or antigen-binding fragment thereof which targets a T-cell cell-surface antigen which is internalized when the targeting moiety binds, such as a CD7 receptor present on T-cells, where the targeting moiety is associated with a binding moiety such as a protein such as a protamine fragment or homologue thereof, or nucleic acid binding domain of a protein, or where the binding moiety associates with the RNA interference, such as siRNA or miRNA.

Alternatively, the present invention relates to a RNAi-complex, such as an siRNA-complex or miRNA-complex which consists essentially of a target moiety, such as an antibody or antigen-binding fragment thereof which targets a T-cell cell-surface antigen which is internalized when the targeting moiety binds, such as a CD7 receptor present on T-cells, where the targeting moiety is associated with a binding moiety such as a protein such as a protamine, or nucleic acid binding fragment or homologue thereof, or nucleic acid binding domain of a protein, or where the binding moiety associates with the RNA interference, such as siRNA or miRNA. In yet another embodiment, the present invention relates to RNAi-complex, such as an siRNA-complex or miRNA-complex consisting of a targeting moiety, a binding moiety and a RNAi molecule.

One can use any targeting moiety in the methods and compositions as disclosed herein which binds to a cell-surface antigen and is internalized when it binds to the cell-surface antigen. In some embodiments, the cell surface antigen targeted by the targeting moiety is any membrane protein present on T-cells, for example but not limited to CD7, LAM-1, CD28 and T cell receptor (TCR), CD3- and ζ-chains, CD4 and CD8 and homologues and variants thereof.

In alternative embodiments, a targeting moiety useful in the methods and compositions as disclosed herein binds to cell-surface antigens or proteins present on tumor cells. Examples include, but are not limited to, tumor-associated antigens (TAAs), the HLA-DR antigen, c-erbB-2 proto-oncogene, MUC1, MAG-1, VEGFR2, pro-vasopressin (pro-VP), TAG-72 (sialyl Tn or STn), STn-KLH, GD3, cancer antigen 125 (CA 125, human ovarian cancer cell surface antigen. (OCCSA), alpha fetoprotein (AFP), and other cancer cell surface antigens which are disclosed in, for example, US20030143237A1, which is incorporated herein by reference.

Antibodies reactive to, or bind specifically to cell surface antigens on T-cells, such as antibodies or fragments that bind to CD7 receptors can be readily raised in animals such as rabbits or mice by immunization with the antigen. Immunized mice are particularly useful for providing sources of B cells for the manufacture of hybridomas, which in turn are cultured to produce large quantities of monoclonal antibodies.

Antibodies provide high binding avidity and unique specificity to a wide range of target antigens and haptens. Monoclonal antibodies useful as targeting moieties in the practice of the present invention include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction of the possibly of adverse immune reactions in a manner similar to that disclosed in European Patent Application No. 0,411,893 A2 which is incorporated herein in its entirety by reference. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule is composed of a variable region (VL) of the light chain and a variable region (VH) of the heavy chain joined via a short peptide spacer sequence. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923, which are incorporated herein in their entirety by reference.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. In some embodiments, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can provide molecules comprising a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, $(scFv)_2$, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used as targeting moieties in accordance with the methods of the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In some embodiments, proteins-binding agents can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively in some embodiments, two or more protein-binding molecules can be administered, for example in some embodiments a protein binding molecule can be an antibody that is conjugated to another, different antibody. Each antibody is reactive with a different target site epitope (associated with the same or a different target site antigen). The different antibodies or antibody fragments with the associated binding moieties and RNAi molecules attached accumulate additively at the desired target site. Antibody-based or non-antibody-based targeting moieties can be employed to deliver the associated binding moiety and its bound RNAi to a target cell or target site.

Binding Moiety

The binding moiety useful in the methods and compositions as disclosed herein binds an RNA interference inducing molecule, for example a siRNA or miRNA. In one embodiment, the binding moiety is a protein or the nucleic acid binding domain of a protein, and the binding moiety is fused to the carboxy portion of the targeting moiety. The location of the targeting moiety may be either in the carboxyl-terminal or amino-terminal end of the construct or in the middle of the fusion protein. Alternatively, the fusion protein may comprise more than one siRNA binding moiety and one or more targeting moieties.

In one preferred embodiment, the binding moiety is the nucleic acid binding domain of a protein selected from the group of nucleic acid binding domains present in proteins selected from the group consisting of protamine, GCN4, Fos, Jun, TFIIS, FMRI, yeast protein HX, Vigillin, Mer1, bacterial polynucleotide phosphorylase, ribosomal protein S3, and heat shock protein. In one preferred embodiment, the binding moiety is the protein protamine or an RNA interference-inducing molecule-binding fragment of protamine. In one embodiment, the binding moiety is a peptide of nine arginines, and is referred to herein as "9R".

In some embodiments, the siRNA complexing agent is protamine or an RNA-binding domain, such as an siRNA-binding fragment of protamine. Protamine is a polycationic peptide with molecular weight about 4000-4500 Da. Protamine is a small basic nucleic acid binding protein, which serves to condense the animal's genomic DNA for packaging into the restrictive volume of a sperm head (Warrant, R. W., et al., Nature 271:130-135 (1978); Krawetz, S. A., et al., Genomics 5:639-645 (1989)). The positive charges of the protamine can strongly interact with negative charges of the phosphate backbone of nucleic acid, such as RNA resulting in a neutral and, as shown here, stable interference RNA protamine complex.

In one embodiment, the protamine fragment useful according to the present invention is encoded by a nucleic acid sequence SEQ ID NO: 1, or a homolog thereof capable of encoding the same amino acids as the SEQ ID NO: 1:

```
                                               (SEQ ID NO: 1)
GCGGCCGCACGCAGCCAGAGCCGGAGCAGATATTACCGCCAGAGACAA

AGAAGTCGCAGACGAAGGAGGCGGAGCTGCCAGACACGGAGGAGAGCC

ATGAGATCTCATCATCACCACCACCATTAA.
```

In one embodiment, the protamine fragment useful according to the present invention is encoded by a nucleic acid sequence SEQ ID NO: 2, or a homolog therefore capable of encoding the same amino acids as the SEQ ID NO: 2:

```
                                               (SEQ ID NO: 2)
GCGGCCGCAATGGCCAGGTACAGATGCTGTCGCAGCCAGAGCCGGAGC

AGATATTACCGCCAGAGACAAAGAAGTCGCAGACGAAGGAGGCGGAGC

TGCCAGACACGGAGGAGAGCCATGAGATCTCATCATCACCACCACCAT

TAA.
```

In one embodiment, the protamine fragment useful according to the present invention is encoded by a nucleic acid sequence SEQ ID NO: 3, or a homolog therefore capable of encoding the same amino acids as the SEQ ID NO: 3:

```
                                               (SEQ ID NO: 3)
GCGGCCGCACGCAGCCAGAGCCGGAGCAGATATTACCGCCAGAGACAA

AGAAGTCGCAGACGAAGGAGGCGGAGCTGCCAGACACGGAGGAGAGCC

ATGAGGTGTTGTCGCCCCAGGTACAGACCGAGATGTAGAAGACACAGA

TCTCATCATCACCACCACCATTAA.
```

In one embodiment, the protamine fragment useful according to the present invention is encoded by a nucleic acid sequence SEQ ID NO: 4, or a homolog therefore capable of encoding the same amino acids as the SEQ ID NO: 4:

```
                                               (SEQ ID NO: 4)
GCGGCCGCACGCAGCCAGAGCCGGAGCAGATATTACCGCCAGAGACAA

AGAAGTCGCAGACGAAGGAGGCGGAGCAGATCTCATCATCACCACCAC

CATTAA
```

In one embodiment, the protamine fragment useful according to the present invention is encoded by a nucleic acid sequence SEQ ID NO: 5, or a homolog therefore capable of encoding the same amino acids as the SEQ ID NO: 5:

```
                                               (SEQ ID NO: 5)
         GCGGCCGCCGGCGGAGGAGGATCTCATCATCACCACCATTAA
```

In one embodiment, the protamine fragment useful according to the present invention is encoded by a nucleic acid sequence SEQ ID NO: 6, or a homolog therefore capable of encoding the same amino acids as the SEQ ID NO: 6:

```
                                               (SEQ ID NO: 6)
GCGGCCGCAATGGCCAGGTACAGATGCTGTCGCAGCCAGAGCCGGAGC

AGATATTACCGCCAGAGACAAAGAAGTCGCAGACGAAGGAGGCGGAGC

AGATCTCATCATCACCACCACCATTAA.
```

In some embodiments, the binding moiety is a full length protamine, which is conjugated with, or associated with, a targeting moiety such as a gp160 antibody or a gp160 binding antibody fragment.

Conjugation of Target Moiety with Binding Moiety

As used herein, the term "associated with" means that one entity is in physical association or contact with another. Thus, a targeting moiety "associated with" a binding moiety can be either covalently or non-covalently joined to the carrier particle. The association can be mediated by a linker moiety, particularly where the association is covalent. The term "association" or "interaction" or "associated with" are used interchangeably herein and as used in reference to the association or interaction of a targeting moiety, e.g., an antibody of fragment thereof with a binding moiety for example a protamine, refers to any association between the targeting moiety with the binding moiety, for example an antibody, either by a direct linkage or an indirect linkage.

The term "linked" refers to two or more entities that are joined by any means known by persons of ordinary skill in the art, for example an antibody or fragment thereof can be linked with another peptide, for example a binding moiety such as a protamine. A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the targeting moiety and/or the binding moiety can be modified by oxidation, hydroxylation, substitution, reduction etc. to provide a site for coupling. It will be appreciated that modification which do not significantly decrease the function of the target moiety, for example antibody, antibody fragment, integrin and/or the binding moiety are preferred.

Alternatively, two or more entities that are joined can be linked by indirect linkage. An indirect linkage includes an association between a targeting moiety, e.g., an antibody of fragment thereof, and a binding moiety, wherein the targeting moiety and the binding moiety are attached via a "linker moiety", e.g., they are not directly linked. Linker moieties include, but are not limited to, chemical linker moieties, or for example a peptide linker moiety. In some embodiments, a linker between a targeting moiety and the binding moiety is formed by reacting the polymer and a linker selected e.g., from the group consisting of p-nitrophenyl chloroformate, carbonyldiimidazole (CDI), N,N'-disuccinimidyl carbonate (DSC), cis-aconitic anhydride, and a mixture of these compounds.

A direct linkage includes any linkage wherein a linker moiety is not required. In one embodiment, a direct linkage includes a chemical or a physical interaction wherein the two moieties, i.e. the targeting moiety and binding moiety interact such that they are attracted to each other. Examples of direct interactions include covalent interactions, non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, a targeting moiety, such as an antibody of fragment thereof and the binding moiety are not linked via a linker, e.g., they are directly linked. In a further embodiment, a targeting moiety and the binding moiety are electrostatically associated with each other.

As used herein, the term "conjugate" or "conjugation" refers to the attachment of two or more entities to form one entity. For example, the methods of the present invention provide conjugation of a targeting moiety of the present invention joined with another entity, for example a binding moiety, for example a protamine. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, the targeting moiety such as an antibody, or antigen binding antibody fragment, can be linked to the binding moiety entity via any suitable means, as known in the art, see for example U.S. Pat. Nos. 4,625,014, 5,057,301 and 5,514,363, which are incorporated herein in their entirety by reference.

A large variety of methods for conjugation of targeting moiety with a binding moiety are known in the art. Such methods are e.g. described by Hermanson (1996, Bioconjugate Techniques, Academic Press), in U.S. Pat. No. 6,180,084 and U.S. Pat. No. 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a targeting moiety or binding moiety can lose efficacy or functionality upon conjugation depending, e.g., on the conjugation procedure or the chemical group utilized therein. However, given the large variety of methods for conjugation, the skilled person is able to find a conjugation method that does not or least affects the efficacy or functionality of the entities to be conjugated.

In some embodiments, a targeting moiety, such as an antibody or variants, derivatives or fragments thereof, can be conjugated by cross-linking. Crosslinking reagents include glutaraldehyde (GAD), bifunctional oxirane (OXR), ethylene glycol diglycidyl ether (EGDE), N-hydroxysuccinimide (NHS), and a water soluble carbodiimide, preferably 1-ethyl-3-(3-dimethylaminopropyl) carbodiimide (EDC). As is known to the skilled artisan, any crosslinking chemistry can be used, including, but not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc. 866 Third Avenue, New York, N.Y. 10022.

Other linkage approaches to conjugate the targeting moiety, for example antibody, or antibody fragment, to a binding moiety, include but are not limited to aminocaproic horse radish peroxidase (HRP) or a heterobifunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homo-biofunctional cross-linkers. Such multistep protocols can offer a great control of conjugate size and the molar ratio of components.

The methods, reagents and references that describe a preparation of a nucleic acid-protamine complex in detail are disclosed in the U.S. Patent Application Publication Nos. US2002/0132990 and US2004/0023902, and are herein incorporated by reference in their entirety. In particular, where a binding moiety is a protamine or protamine like agent, the methods, regents and reference that describe the preparation of protamine associated with a targeting moiety, such as an antibody or antibody fragment are disclosed in U.S. Provisional Application 60/957,023 and International Patent Application US2007/012152, which are incorporated herein in their entirety by reference.

As used herein, "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see below) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

Determination of homologs of the genes or peptides of the present invention can be easily ascertained by the skilled artisan. The terms "homology", "identity" and "similarity" refer to the degree of sequence similarity between two optimally aligned peptides or between two optimally aligned nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectively. A sequence which is "unrelated" or "non-homologous" shares less than 40% identity, though preferably less than 25% identity with a sequence of the present application.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" if the change does not reduce the activity of the peptide (i.e. the ability of an binding moiety to bind or associate with a nucleic acid). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents. Conservative amino acid substitutions are well known in the art, for example as disclosed in Dordo et al, J. Mol Biol, 1999, 217, 721-739 and Taylor et al, J. Theor. Biol. 119 (1986); 205-218 and S. French and B. Robson, J. Mol. Evol. 19 (1983)171. Conservative amino acids encompassed for use in the methods as disclosed herein include conservative substitutions that are suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

As used herein, the term "non-conservative" refers to substituting an amino acid residue for a different amino acid residue that has different chemical properties. The non-conservative substitutions include, but are not limited to aspartic acid (D) being replaced with glycine (G); asparagine (N) being replaced with lysine (K); or alanine (A) being replaced with arginine (R). "Insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

In one embodiment, the term "protamine homolog" refers to an amino acid sequence that has at least 40% homology to the full length amino acid sequence of the protamine polypeptide of SEQ ID NO:1 and which binds or associates with RNA. As a non-limiting example, a protamine fragment homologue is at least 40% homologous to the full length amino acid sequence of SEQ ID NO:1, more preferably at least about 50% homologous, or at least about 60% homologous, or at least about 70% homologous, or at least about 75% homologous, or at least about 80% homologous, or at least about 85% homologous, or at least about 90% homologous, or at least about 95% homologous. As discussed above, the homology is at least about 40% to 99% and all integers in between (i.e., 45%, 55%, 60%, 70%, 75%, 80%, 85%, 90%, 95%, 98%, etc.).

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or 1) or residue occurs in both sequences to yield the number of matched positions, dividing the number of matched positions by the total number of positions in the comparison window (i.e., the window size), and multiplying the result by 100 to yield the percentage of sequence identity.

In one embodiment, the term "protamine homolog" refers to an amino acid sequence that has at least 40% identical to the full length amino acid sequence of the protamine polypeptide of SEQ ID NO:1 and which binds or associates with RNA. As a non-limiting example, a protamine fragment homologue is at least 40% identical to the full length amino acid sequence of SEQ ID NO:1, more preferably at least about 50% identical, or at least about 60% identical, or at least about 70% identical, or at least about 75% identical, or at least about 80% identical, or at least about 85% identical, or at least about 90% identical, or at least about 95% v. As discussed above, the identity is at least about 40% to 99% and all integers in between (i.e., 45%, 55%, 60%, 70%, 75%, 80%, 85%, 90%, 95%, 98%, etc.).

The term "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the; percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information interne web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

Uses

In some embodiments, the siRNA complexes as disclosed herein are useful for the treatment, including prophylactic treatment of a T-cell related disease or disorder. For example, as disclosed in the Examples, the siRNA complexes comprising anti-HIV-1 siRNA and other therapeutic siRNA are useful for inhibiting HIV infection or for treating HIV-infected cells to maintain T-cell survival.

The siRNA complexes as disclosed herein comprise a targeting moiety which targets T-cells, and therefore the siRNA complexes as disclosed herein are useful for delivering siRNAs to T cells to treat any T-cell disease or disorder, where a targeted reduction in the expression of one or more genes can provide therapeutic benefit.

One example of a T-cell disease or disorder is a T-cell immune disease, such as HIV (human immune deficiency virus) where the siRNA complexes can be associated with RNAi molecules directed to maintaining T-cell survival. In such an embodiment, as an illustrative example only the siRNA-complex as disclosed herein can comprise a siRNA aimed at inhibiting cell death or pro-apoptotic genes, such as siRNA molecules which gene-silence pro-apoptotic genes such as BAX, Smac/DIABLO, Fos, FasL etc. In some embodiments, the siRNA molecules can be designed to target gene silencing of various different pro-apoptotic genes which are commonly known by persons of ordinary skill in the art, such as, but not limited to Hsp90; TNFα; DIABLO; BAX; inhibitors of Bcl-2; Bad; poly ADP ribose polymerase-1

(PARP-1): Second Mitochondrial-derived Activator or Caspases (SMAC); apoptosis inducing factor (AIF); Fas (also known as Apo-1 or CD95); Fas Ligand (FasL) or variants or fragments thereof.

In alternative embodiments, another example of a T-cell disease or disorder is a T-cell proliferative disease, such as T-cell lymphoma where the siRNA complexes can be directed at inducing T-cell death or apoptosis. In such an embodiment, as an illustrative example only the siRNA-complex as disclosed herein comprises an siRNA aimed at inhibiting survival genes, such as a pro-apoptotic siRNA which gene-silences a pro-survival gene such as Bcl-2, Hsp27, Hsp70, Bcl-XL, inhibitors of apoptosis (IAP) proteins, etc.

Viruses

In alternative embodiments, the siRNA complexes as disclosed herein are useful for the treatment, including prophylaxis treatment of any virus related disease or disorder. Examples of virus related diseases or disorders include, but are not limited to AIDS/HIV; avian flu; SARS; Hepatitis type A; Hepatitis type B; Hepatitis Type C; influenzia; varicella; adenovirus, HSV-2; HSV-II; rinderpest rhinovirus; echnovirus; rotavirus; respiratory syncytial virus; papilloma virus; papova virus; cytomegalovirus; echinovirus; abovirus; hantavirus; coxsackie virus; measles virus; mumps virus; rubella virus; polio virus; HIV-I, HIV-II; avian and/or bird flu virus; ebola virus; other viruses. Other viruses include, for example, but are not limited to Herpes simplex virus type-1, Herpes simplex virus type-2, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B. Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Simian humanodeficiency virus, Human T-cell Leukemia virus type-1, Hantavirus, Rubella virus, Simian Enmunodeficiency virus, Human Immunodeficiency virus type-1, and Human Immunodeficiency virus type-2. In some embodiments, the siRNA complexes as disclosed herein are useful for the treatment, including prophylactic of a subject infected with HIV. Prevention of virus induced tumors is also contemplated using the targeted complexes as disclosed herein. For example, targeting cells infected with human papillioma virus (HPV) can prevent development of cervical cancer caused by HPV infection.

Cancer

As used herein, the term "tumor" means a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

Blood vessels provide conduits to metastasize and spread elsewhere in the body. Upon arrival at the metastatic site, the cancer cells then work on establishing a new blood supply network. One approach to the treatment of cancer using complexes as disclosed herein is to target cancer cells using tumor antigens expressed on their cell surface, with RNA interference aimed at pro-angiogenic factors or genes. Specific candidates would include, for example genes expressing VEGF, bFGF and other pro-angiogenic factors produced by tumor cells.

In this approach administration of the compositions as disclosed herein is useful to treat any cancer with a primary tumor site, which can optionally have a secondary tumor site. Such an approach serves to prevent and limit the progression of the disease. Any solid tumor that requires an efficient blood supply to keep growing is a candidate target. For example, candidates for the treatment described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In some embodiments, where the compositions are used for the treatment or prevention of cancer, the siRNA can alternatively be used to target oncogenes or proto-oncogenes, for example but no limited to target polynucleotides such as, but not limited to, v-fms; v-myc; v-src; v-abl; v-erb; v-erba; v-fos; M1 protein; virus like particles (VPL). The term "oncogene" as used herein refers to a nucleic acid sequence encoding, or polypeptide, of a mutated and/or overexpressed version of a normal gene that in a dominant fashion can release the cell from normal restraints on growth. Oncogenes can alone or in concert with other changes or genes, contribute to a cell's tumorigenicity. Examples of oncogenes include; gp40 (v-fms); p21 (ras); p55 (v-myc); p65 (gag-jun); pp 60 (v-src); v-abl; v-erb; v-erba; v-fos etc. A "proto-oncogene" or "pro-oncogene" refers to the normal expression of a nucleic acid expressing the normal, cellular equivalent of an oncogene; typically these genes are involved in the signaling or regulation of cell growth. Examples include c-myc, c-fos, c-jun etc.

The terms "treat" or "treatment" refer to both therapeutic treatment and prophylactic or preventative measures, wherein the object is to prevent or slow the development of the disease, such as slow down the development of AIDS or the spread of cancer. Treatment is generally 'effective' if one or more symptoms or clinical markers are reduced as that term is defined herein. Alternatively, treatment is "effective" if the progression of a disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with HIV infection, or in some embodiments, those already diagnosed with cancer as well as those likely to develop secondary tumors due to metastasis.

Pharmaceutical Compositions

In some embodiments, an siRNA complex as disclosed herein can be administered to a subject using any delivery system such as topical administration, subcutaneous, intramuscular, intraperitoneal, intrathecal and intravenous injections, catheters for delivering the siRNA complexes into, for example, a specific organ, such as brain, liver, heart or kidneys, or into, for example, a specific location having been affected with malignant growth or viral infection. In some embodiments, the siRNA complex as disclosed herein comprising a targeting moiety and a binding moiety, such as a protamine or fragment thereof, and associated RNAi molecule is administered to a subject in a composition, such as a pharmaceutical composition.

When used in the context of siRNA complexes, the terms "composition" or "pharmaceutical composition" are used interchangeably herein, and refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art can be used. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

The term "pharmaceutically acceptable carrier" means any pharmaceutically acceptable means to mix and/or deliver the targeted delivery composition, for example targeted siRNA complex to a subject, for example any pharmaceutically acceptable material, composition or vehicle, such as a liquid or solid filler, diluent, excipient, solvent or encapsulating material, involved in maintaining the complex's activity, facilitating delivery, to a subject, or carrying or transporting the siRNA-complex as disclosed herein from one organ, or portion of the body, to another organ, or portion of the body. Each carrier must be "acceptable" in the sense of being compatible with the other ingredients of the formulation and must be compatible with administration to a subject, for example a human. For the clinical use of the methods of the present invention, the siRNA-complexes are formulated into pharmaceutical formulations for oral, rectal, vaginal, parenteral, topical, intravenous or other mode of administration. The pharmaceutical formulation contains a compound as disclosed herein in combination with one or more pharmaceutically acceptable carriers. The carrier may be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration.

The term "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration" and "administered peripherally" as used herein mean the administration of a compound, drug or other material other than directly into the desired point of action, such that it enters the animal's system and, thus, is subject to metabolism and other like processes. A non-limiting example is subcutaneous or intravenous administration.

As used herein, the terms "administering," and "introducing" are used interchangeably and refer to the placement of the pharmaceutical composition comprising a targeting moiety, such as an antibody and a binding moiety, such as a protamine and associated agents, such as RNAi as described herein into a subject by a method or route which results in at least partial localization of the agents at a desired site. The agents described herein can be administered by any appropriate route which results in an effective treatment in the subject.

In the preparation of pharmaceutical formulations containing the siRNA-complex of the present invention in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention in vegetable oil, fat, or other suitable vehicle for soft gelatin capsules. Hard gelatin capsules may contain granules of the active compound. Hard gelatin capsules may also contain the siRNA-complex including the target moiety and the RNA-binding moiety as well as the target siRNA in combination with solid powdered ingredients such as lactose, saccharose, sorbitol, mannitol, potato starch, corn starch, amylopectin, cellulose derivatives or gelatin.

Dosage units for rectal or vaginal administration may be prepared (i) in the form of suppositories which contain the active substance, i.e. the siRNA-complex, mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The methods of the present invention to deliver RNA interference can also be used to deliver RNA interference orally in granular form including sprayed dried particles, or complexed to form micro or nanoparticles.

The subject or individual as referred to herein and throughout the specification includes mammals, such as murine, specifically mice and rats, bovine, and primates, such as human.

The term "in vivo delivery" as used herein means delivery of the siRNAs into a living subject, including a human. The term "in vitro delivery" as used herein means delivery of siRNAs into cells and organs outside a living subject.

The term "effective amount" as used herein refers to the amount of therapeutic agent of pharmaceutical composition to alleviate at least one or more symptom of the disease or disorder, and relates to a sufficient amount of pharmacological composition to provide the desired effect. The phrase "therapeutically effective amount" as used herein, e.g., the siRNA complex as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with a T-cell disease or a cancer-mediated condition when administered to a typical subject who has a T-cell disease or a cancer.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated. Examples of different T cell diseases include a where the affected subject has a deficiency in T cells or a reduced level of T cells (for example in subjects affected with T-cell diseases such as HIV), or alternatively where the affected subject has increased proliferation of T cells or an increased level of T cells (for example a T-cell lymphoma). A therapeutically effective amount as the term is used herein need not eradicate the disease, for example need not eradicate the HIV virus or, in alternative embodiments a tumor or neoplasm.

With reference to the treatment of a subject with a HIV infection, the term "therapeutically effective amount" refers to the amount that is safe and sufficient to prevent or delay the decrease in T-cells or development of acquired immunodeficiency syndrome (AIDS) in HIV infected subjects. Efficacy for any given formulation or composition can also be judged using an experimental animal model of HIV, for example as disclosed herein in the Examples, akin to cells transfected with HIV or the humanized mouse model as disclosed herein, which essentially replicates the human immune environment in the mouse, and thus the results are expected to be predictive of a similar outcome in human subjects. In alternative embodiments, the compositions can be tested on a biological sample, such as blood from a seripositive HIV patient as disclosed in the Examples. When using an experimental animal model, efficacy of treatment is evidenced when a reduction in a symptom of the HIV infection, for example an increase in the number of T-cells or a slowing or cessation of the rate of decrease of T-cell reduction occurs earlier in treated, as compared to untreated animals. By "earlier" is meant that the T-cell level increase or the slowing or cessation of the rate of T-cell decrease occurs at least 5% earlier, but preferably more, e.g., one day earlier, two days earlier, 3 days earlier, or more. Thus, a therapeutically effective amount useful for the treatment of a subject infected with HIV will slow the rate of T-cell loss in a subject as compared to a rate without the therapeutic agent, and in some embodiments, increase the number of T-cells to the level which would be present in a healthy unaffected subject With reference to the treatment of a subject with a cancer, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term treating when used in reference to a cancer treatment is used to refer to the reduction of a symptom and/or a biochemical marker of cancer, for example a reduction in at least one biochemical marker of cancer by at least 10% would be considered an effective treatment. Examples of such biochemical markers of cancer include CD44, telomerase, TGF-α, TGF-β, erbB-2, erbB-3, MUC1, MUC2, CK20, PSA, CA125 and FOBT. A reduction in the rate of proliferation of the cancer cells by at least 10% would also be considered effective treatment by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as affective treatments by the methods as disclosed herein. Thus, a therapeutically effective amount for the treatment of a subject with a T-cell lymphoma is an amount that will reduce the level of T-cell proliferation, and in some embodiments reduce the number of T-cells in the affected subject, for example reduction of T-cell levels to a level which would be present in a normal healthy or unaffected subject. In some embodiments, it is preferred, but not required that the therapeutic agent actually kill the tumor.

A therapeutically effective dose for any particular subject will depend upon a variety of factors including, for example the disorder being treated and the severity of the disorder; the activity and specificity of the RNAi molecule being delivered; the specific target gene of the RNAi molecule; the half-life and turn over of the protein expressed by the target gene; the expression level of the target gene; the age, body weight, general health, sex and diet of the patient; the time of administration, route of administration, and rate of excretion of the specific compound employed; the duration of the treatment; drugs used in combination or coincidental with the compositions and formulations as disclosed herein; and like factors well known in the medical arts. For example, it is well within the skill of the art to either start doses of the compound at levels lower than required to achieve the desired therapeutic effect and to gradually increase the dosage until the desired effect is achieved, or start doses of the compound at high levels and to gradually decrease the dosage until the desired effect is achieved, as appropriate for the care of the individual patient or subject.

The compositions as disclosed herein can also be administered in prophylactically or therapeutically effective amounts. The formulations and compositions as disclosed herein can be administered along with a pharmaceutically acceptable carrier. A prophylactically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

In addition, the amount of each component to be administered also depends upon the frequency of administration, such as whether administration is once a day, twice a day, 3 times a day or 4 times a day, once a week; or several times a week, for example 2 or 3, or 4 times a week.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%. The present invention is further explained in detail by the following examples, but the scope of the invention should not limit thereto.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention. The Examples presented herein relate to methods, compositions and formulations of RNAi complex delivery system which delivers RNAi molecules to target cells, where the RNAi complex comprises of a targeting moiety, such as an antibody or antigen binding antibody fragment which targets cell surface antigens which are internalized upon binding of the targeting moiety, a binding moiety, such as a protamine fragment, which binds a RNAi molecule, and an RNAi molecule.

Methods siRNAs:

siRNAs used in the studies included those directed to firefly luciferase (siLuc)[14], the HIV genes Vif[5] and Tat[26], the coreceptor gene CCR57 and the human T cell receptor CD46. All siRNAs were obtained from Dharmacon, Inc.

Purification of scFvCD7 Single Chain Antibody and Conjugation to Oligo-9R:

The coding sequence of scFvCD7 was PCR amplified from the pAK400scFvCD7-GFP construct obtained from Dr. George Fey[17] using a primer that introduced a C-terminal cysteine residue in frame with the scFv sequence to enable subsequent disulfide conjugation with a positively charged siRNA binding moiety. PCR amplified scFvCD7Cys was cloned into the pET 26b(+) vector (Novagen Inc.). The recombinant protein was purified to homogeneity by FPLC using Bio Scale Mini Profanity immobilized metal affinity chromatography (Bio-Rad) and then refolded essentially as described[27]. Cell specific binding was verified by pre-incubating $5 \times 10^5$ CD3+ T cells purified from healthy donor PBMC (Peripheral Blood Mononuclear Cells) for 30 min on ice with purified scFvCD7Cys (20 μg/ml). Cells were then washed and stained with anti-human CD7-PE, CD3-FITC and CD4-PECy5 antibodies (BD-Pharmingen) followed by flow cytometric analysis. In some experiments the scFvCD7-Cys treated cells were cultured at 37° C. in complete medium and stained at different times for surface CD7 expression with anti-CD7PECy5.

The refolded scFvCD7Cys was concentrated to 1 mg/ml and mixed with Cys(Npys)-(D-Arg)9 peptide (9R, Anaspec) at the same concentration in 0.1M phosphate buffer (pH 5.5) at a molar ratio of 10 to 1 and conjugation performed by a gentle stirring for 4 h at room temperature[28]. Typically, conjugation efficiencies of around 75% were achieved as measured by a thiol and sulfide quantization assay kit (Molecular probes, data not shown). The final reactants were dialyzed against PBS using membrane MWCO 10,000 to remove unbound 9R and for use in further experiments.

siRNA Binding and Silencing Experiments:

For gel mobility shift assays, 100 pmole siRNA was incubated with CD7scFv/9R at the indicated concentrations for 15 min, electrophoresed on 1% agarose gels and stained with ethidium bromide. To test antibody-mediated delivery and silencing, PBMC derived CD3+ T cells, CD19+ B cells or CD14+ monocytes differentiated in vitro into monocyte derived macrophages were seeded in 96 well-plates at $2 \times 10^5$ cells/well and treated a day later with scFvCD7-9R-siFITC (100 pmol siRNA) for 4 h at a molar ratio 5:1, determined to be optimal by experimentation. After washing, cells were incubated for an additional 16 h at 37° C. and subjected to flow cytometric analysis. For silencing experiments also, a molar ratio of scFvCD7-9R/siRNA of at least 5:1 was found to be effective. scFvCD7-9R was complexed with 400 pmole siRNA targeting human CD4 was added to $5 \times 10^5$ PHA-stimulated PBMC and surface CD3, CD4 and CD8 levels assessed after 60 h of treatment by flow cytometry.

To assess possible toxicity of scFvCD7-9R complexes, scFvCD7-9R/siLuc treated or control PBMC were incubated for 24 h at 37° C. and then stained with Annexin V. Treatment with Staurosporine at 1 μM was used as positive control. In separate experiments, the same PBMC were treated in triplicate wells with either PHA (4 μg/ml) or Dynabeads CD3/CD28 T cell Expander (1 bead per cell) for 3 days, pulsed with 3H-thymidine at 1 μCi per well for 18 h. The cells were then harvested and the incorporated counts measured in a Beckman Coulter LS 6500 scintillation counter.

Generation of Hu-PBL and Hu-HSC Mice:

NOD.cg-PrkdcscidIL2rgtm/Wjl/Sz (Nod/SCID/IL2rγ−/−) mice used for human cell reconstitution were raised by Dr. Leonard Shultz at the Jackson Laboratory, Bar Harbor, Me. Hu-PBL mice were generated as described[29,30]. Briefly, PBMC ($10^7$) freshly obtained by Ficoll gradient centrifugation from heparinized blood of a healthy HIV-seronegative donor was suspended in RPMI (0.5 ml) and infused intraperitoneally into 4-6 week old mice. In some experiments, 5 million PBMC obtained from a HIV-seropositive donor were used similarly. All mice were tested for positive engraftment by 3-5 days after transplantation by staining PBMC obtained by retro-orbital bleeds for the pan leukocyte marker CD45. As used herein, "PBL" refers to peripheral blood lymphocytes, and "HSC" refers to hematopoietic stem cells, and Hu-HSC mice refers to a novel humanized mouse model which has been reconstituted with human hematopoietic stem cells (Zhang et al., Blood, 2007, 109; 2978-2981).

Humanized Hu-HSC were prepared essentially as described[10]. After irradiation at 100 rads, 1-2 day old neonatal mice were injected intravenously with T cell depleted cord blood cells containing $3 \times 10^4$ CD34+ cells per mouse. Transplanted mice were tested for positive engraftment as described above 12 weeks post reconstitution. All experimental protocols were approved by the Ethics Review Committee for Animal Experimentation.

Treatment of Humanized Mice with scFvCD7/siRNA Complexes:

After ascertaining human T cell engraftment by staining for CD3, CD4 and CD8 positive T cells, mice were i.v. infused at the indicated times with scFvCD7-9R/siRNA complexes at a 5:1 molar ratio at a dose of 50 μg siRNA per injection in 5% glucose in a volume of 200 μl. In infection experiments, Hu-PBL mice were inoculated on day 16 post transplantation with 10000TCID50 of HIV$_{BaL}$ in a 100 μl volume. The experimental regimen followed for scFvCD7-9R/siRNA administration for each experiment is illustrated in the corresponding figure. Hu-PBMC recovered from the mice were stained with hCD3-FITC, hCD4-PECy5 and hCD8-PE antibodies (Pharmingen) and analyzed by flow cytometry. CD4 T cell ratios were calculated as a ratio of the entire CD3 population (CD4+CD3+:CD3+). Plasma p24 levels were measured using the p24 antigen ELISA kit (NEN, Perkin Elmer). Viral load in EDTA-treated plasma samples were determined with the Amplicor test (Roche diagnostics).

HIV-1 Infection of Primary Cells In Vitro:

Human cells isolated from reconstituted mice were cultured at 0.2 million cells per well in 96 well plates in RPMI containing 20% serum in the presence of PHA (4 μg/ml) for 3 days prior to infection with HIV-1$_{BaL}$ or HIV-1IIIB at an moi of 3 and supernatants assayed by p24 ELISA (NEN, Perkin Elmer) at the indicated times.

Statistical Analyses:

All statistical analyses comparing 2 groups of data were performed by Mann Whitney as well as the Students t test. The Kruskall-Wallis test followed by the Dunn's post test was used for more than 2 groups. P<0.05 was considered significant.

Example 1

The inventors have previously demonstrated that the inclusion of 9 arginine residues to a neuronal cell targeting peptide allowed siRNA binding, enabling targeted delivery to neuronal cells[14]. The inventors demonstrate herein efficient and effective targeted delivery of siRNA into human T cells. Antibodies to the T cell-specific surface protein CD7 are efficiently internalized and have been used for delivery of toxins to T cell lymphomas in both preclinical studies and clinical trials, the inventors used a CD7-specific single chain antibody for T cell targeting[15-17]. The antibody was modified to contain an additional Cys residue at the C-terminal end (scFvCD7Cys) to permit conjugation to nona-d-arginine (9R) peptide.

Figure 5B:
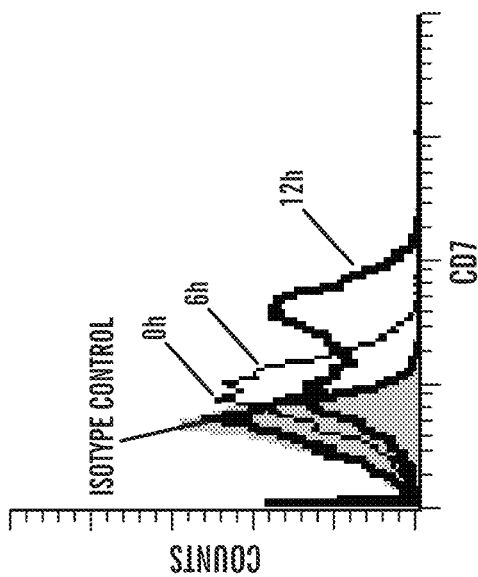
Figure 5A:
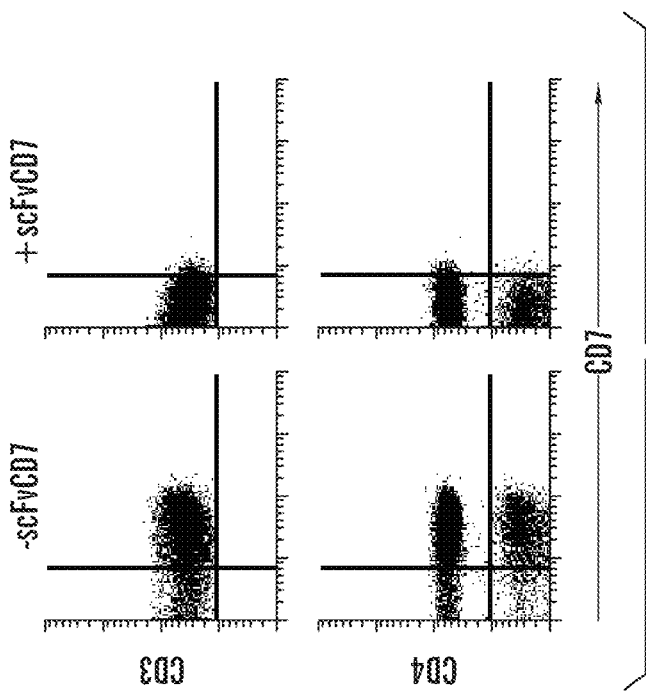
Figure 5D:
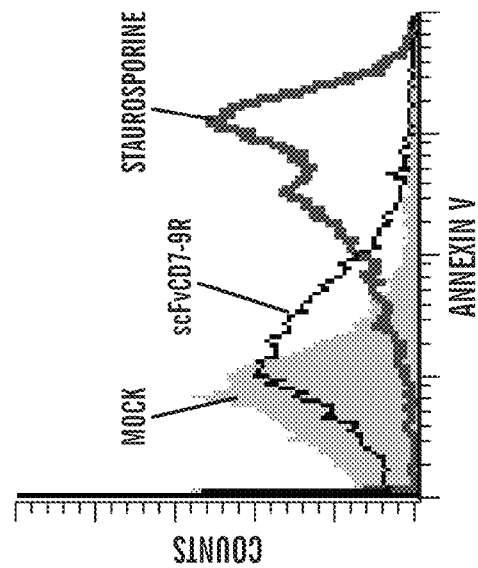
Figure 5C:
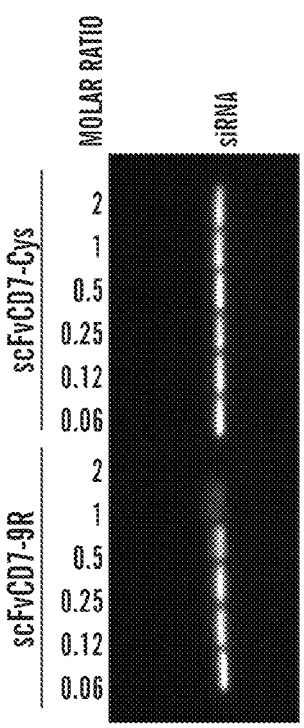

Recombinant scFvCD7Cys was purified from bacterial lysates and verified for specific ligand binding by its ability to the inhibit binding of PE-labeled anti-CD7 antibody to Jurkat cells (data not shown) or CD3+ T cells purified from human PBMC (FIG. 5a). This inhibition was reversed completely by 12 h, suggesting rapid internalization and turnover of the receptor (FIG. 5b). To enable siRNA binding, the inventors chemically conjugated a 9R peptide at the C-terminal of scFvCD7Cys (scFvCD7-9R) and ascertained conjugation by quantitative measurement of free thiol groups (data not shown). Dose-dependent siRNA binding ability of scFvCD7-9R was confirmed in an electrophoretic gel mobility-shift assay (FIG. 5c). In initial studies, the inventors discovered that scFvCD7-9R could mediate delivery of FITC-siRNA into CD7-positive Jurkat T cells but not CD7-negative cell lines and a siRNA: antibody molar ratio of at least 1:5 was required for efficient delivery (data not shown). Further, scFvCD7-9R could deliver FITC-siRNA very effectively into purified human CD3$^+$ T cells with transfection efficiencies of nearly 95% under the conditions tested with no apparent toxicity (FIG. 1a, upper panels). T cell-specific delivery of siRNA was also confirmed by the absence of siRNA in similarly treated CD7-negative B cells (CD19) and monocyte-derived macrophages (CD14) (FIG. 1a, lower panel).

Figure 1B:
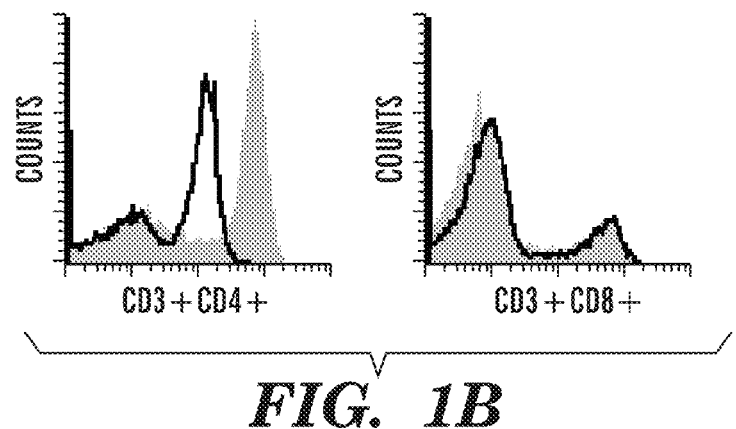

To test if scFvCD7-9R delivered siRNA silences target gene expression, the inventors treated PMA-activated human PBMC with scFvCD7-9R/siCD4 complexes and examined surface CD4 expression 48 h later. The mean fluorescent intensity (MFI) of CD4 was reduced by almost a log on CD3$^+$ T cells (FIG. 1b). The silencing was specific since CD8 expression remained unaffected. No reduction in CD4 expression was observed with scFvCD7-9R/siLuc, siCD4 alone or with 9R or scFvCD7Cys (data not shown). scFvCD7-9R/siRNA treatment was non-toxic as assessed by lack of Annexin-V positivity in treated cells (FIG. S1d) as well as the normal proliferative response of T cells to stimulation with PHA or anti-CD3/CD28 beads after antibody treatment (FIG. 5e). Thus, scFvCD7-9R can be used for siRNA delivery and specific gene silencing in primary T cells without detectable deleterious effects.

Figure 1C:
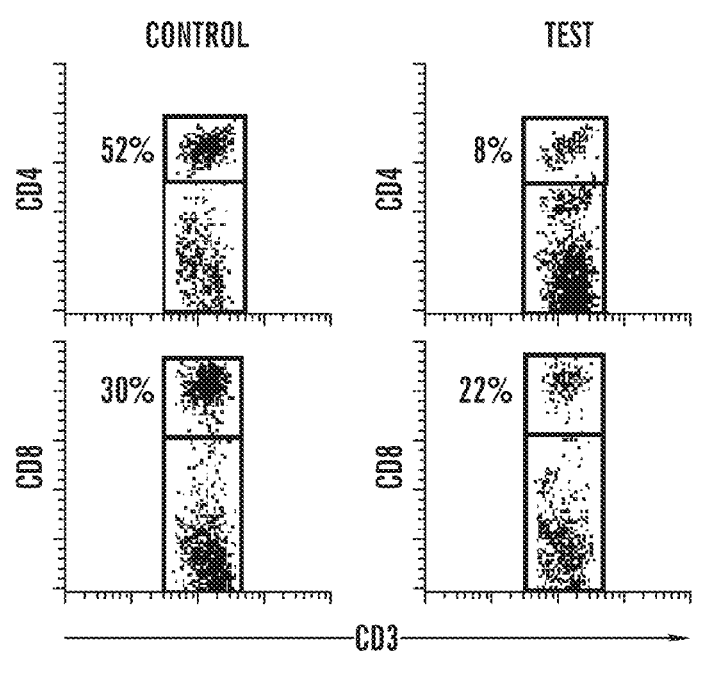
Figure 6A:
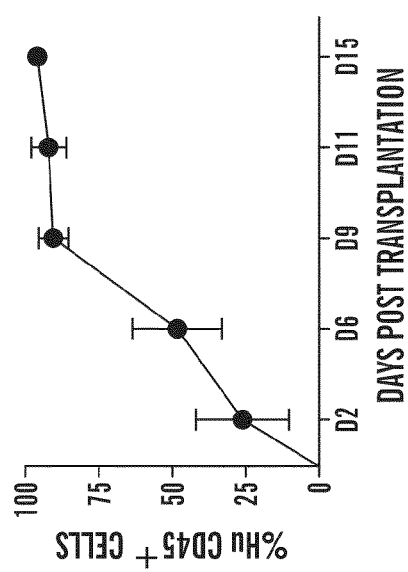
FIGS. 6A-6C show human cell repopulation in NOD/SCID/IL2rγ$^{-/-}$ mice after engraftment with PBMC (Hu-PBL) or CD34$^+$ HSC (Hu-HSC).

The ability of scFvCD7-9R to deliver siRNA into T cells in vivo was studied in the NOD/SCIDIL2r$\gamma^{-/-}$ Hu-PBL mouse model, which supports high level of human peripheral blood leukocyte engraftment[18] (FIG. 6a). In PHA-activated T cells, surface CD7 expression was completely restored by 12 h after treatment with scFvCD7, indicating that repeated administration of scFvCD7-9R is possible (FIG. 5b). Thus, Hu-PBL mice were injected intravenously with scFvCD7-9R/siCD4 complexes consecutively on 2 days and CD4 expression on peripheral blood T cells examined by flow cytometry 60 h after the last injection. CD4$^+$ T cell levels were significantly reduced in scFvCD7-9R/siCD4 treated, but not in control siLuc-treated mice (FIGS. 1c and d). However, CD8$^+$ T cell levels remained unchanged, confirming that silencing was restricted to the targeted gene. Cells isolated from other organs like liver and spleen also showed knockdown levels similar to that in peripheral blood mononuclear cells (PBMC) (FIG. 1d). When PBMC from treated mice were infected with HIV IIIB ex vivo, HIV-1 p24 levels were significantly reduced in culture supernatants, confirming reduced permissibility to viral infection after knockdown of CD4 expression (FIG. 5f). The inventors also determined the duration of gene silencing in vivo. For this, mice were treated with scFvCD7-9R/CD4siRNA three times at 16 h intervals and CD4 expression levels on serial samples of peripheral T cells analyzed by flow cytometry. Silencing was maximal during the first 3 days, but was progressively lost and by day 9, CD4 expression had returned to 70% of normal levels (FIG. 1e).

Example 2

Figure 2A:
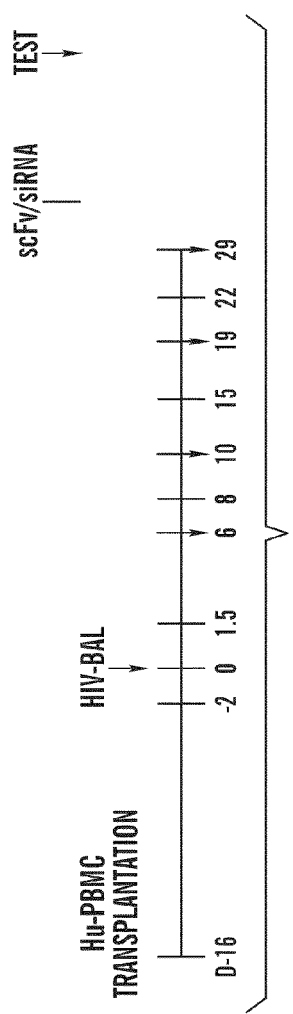
FIGS. 2A-2D shows that i.v. treatment with siRNAs complexed to scFvCD7-9R prevents HIV infection in Hu-PBL mice.
Figure 2B:
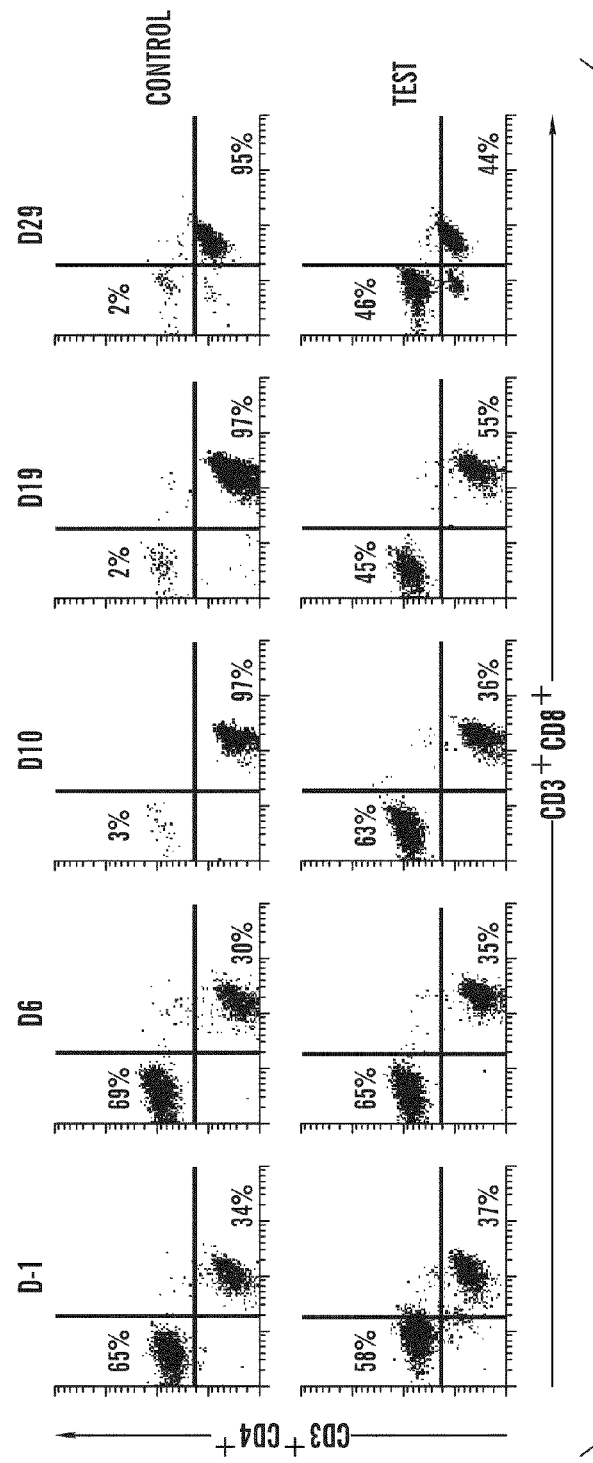
Figure 2C:
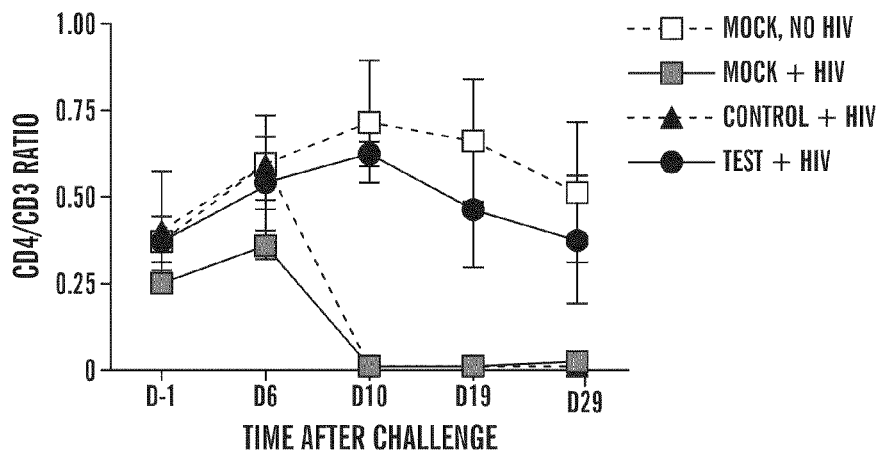
Figure 2D:
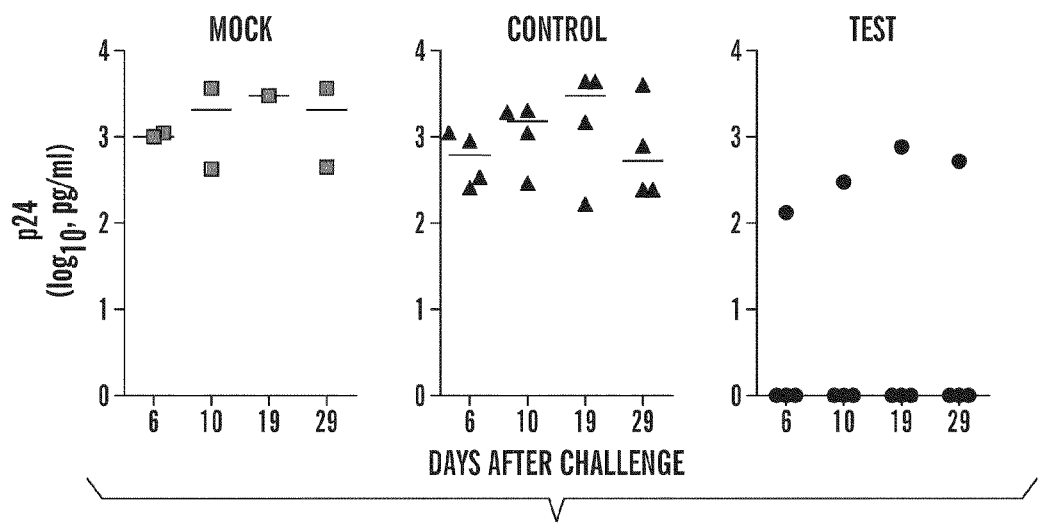

Next the inventors tested the therapeutic potential of scFvCD7-9R mediated siRNA delivery in HIV infection. Human T cells in Hu-PBL mice express high levels of CCR5 and are susceptible to R5-tropic strains of HIV[18,19], with infection resulting in a progressive loss of CD4 T cells that recapitulates human infection[20]. A combination of siRNAs targeting cellular co-receptor CCR5 and 2-3 conserved viral gene sequences has been proposed as an optimal strategy to prevent the emergence of escape mutants[21]. Thus, 14 days after reconstitution, Hu-PBL mice (reconstituted with HIV-naïve human PBL) were treated with CCR5 siRNA to block viral entry, challenged with HIV$_{BaL}$ two days later and further treated by weekly administrations of a combination of siRNAs targeting CCR5 (to prevent viral spread) and conserved target sequences in the viral vif and tat genes (to block viral replication) (FIG. 2a). All siRNAs were complexed to scFvCD7-9R prior to injection. Control HIV-infected mice were treated with scFvCD7-9R/siLuc complex. As early as 10 days post infection, CD4 T cell levels declined precipitously in all of the mock- and control siLuc-treated mice, with CD4$^+$ CD3$^+$ T cell percentages dropping to as low as 2% and CD8$^+$ CD3$^+$ percentages concomitantly increasing to above 95% (FIGS. 2b and 2c). In sharp contrast, in 3/4 relevant siRNA treated mice, the CD4 T cells remained essentially normal even 4 weeks post infection (FIGS. 2b and 2c). Consistent with changes in the CD4 T cell levels, viral replication (as assessed by serial measurement of serum p24 antigen levels by ELISA) was high in the mock- and control siLuc-infected mice, but undetectable in 3/4 relevant siRNA-treated mice (FIG. 2d). In the single test mouse that was not protected, the peripheral CD4 T cell loss exhibited slower kinetics (CD4/CD3 ratio of 0.6 at day 10 as opposed to a mean value of 0.016 in control mice) and correspondingly, the serum p24 levels tended to be lower compared to mean values in the control mice. Taken together, the inventors have demonstrated that treatment with scFvCD7-9R/siRNA can prevent HIV replication and the consequent CD4 T cell loss in vivo. Because the humanized mouse model essentially replicates the human immune environment in the mouse, the results are expected to be predictive of a similar outcome in human subjects.

Example 3

Figure 3A:
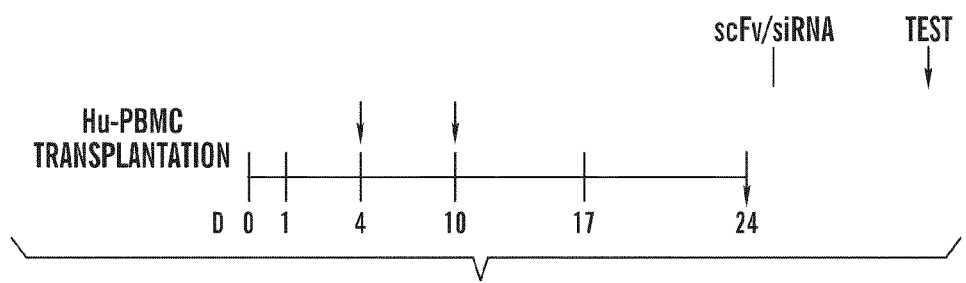
FIGS. 3A-3D shows that i.v. treatment with siRNA/scFvCD7-9R complexes prevents CD4 T cell loss and HIV-1 amplification in mice reconstituted with HIV-seropositive donor PBMC.
Figure 3B:
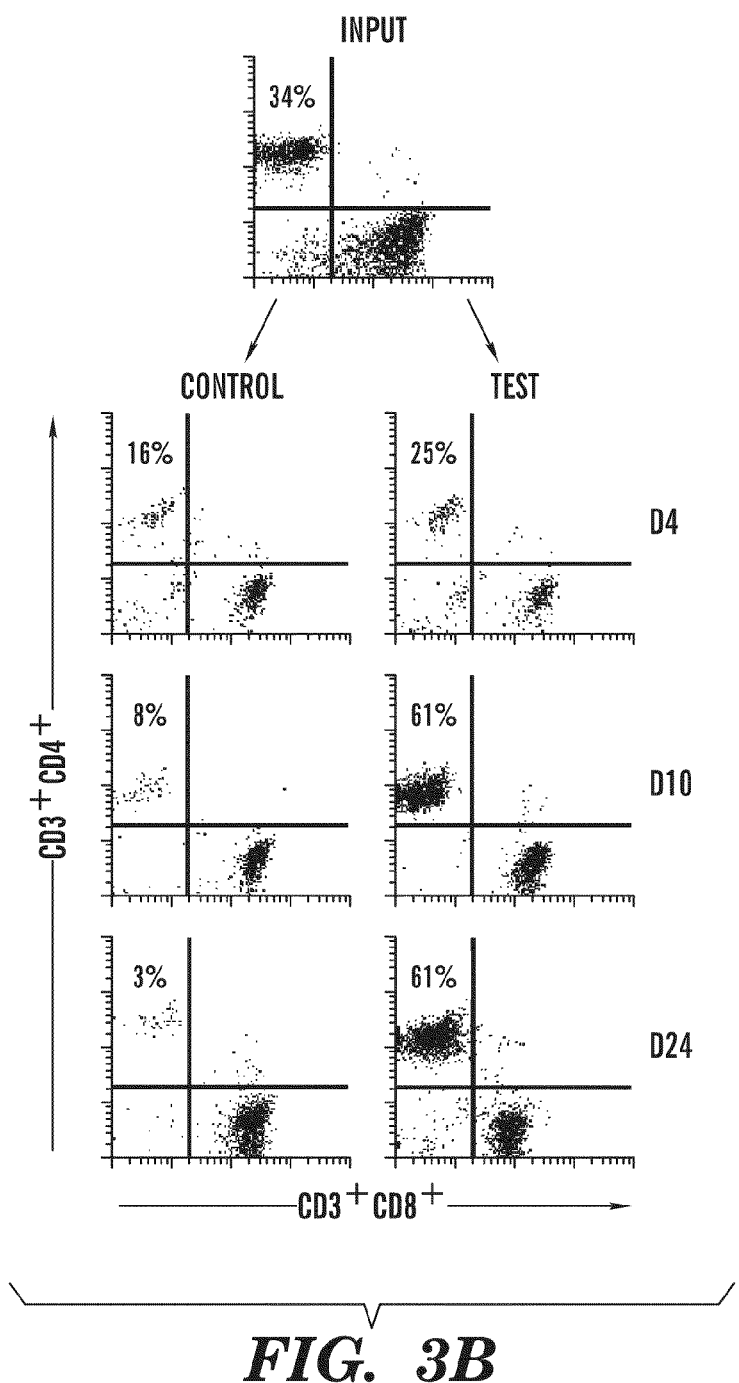
Figure 3C:
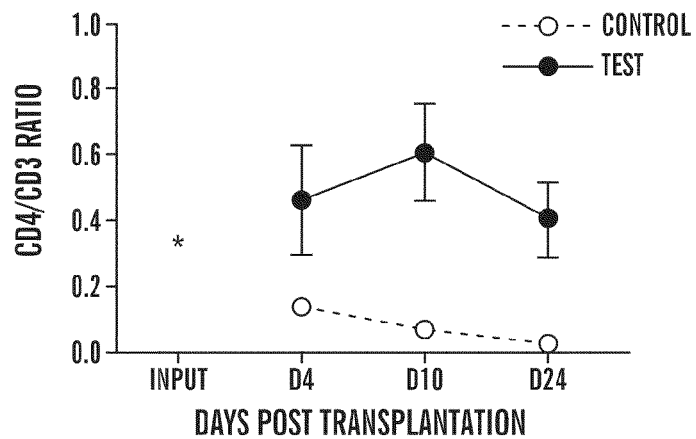
Figure 3D:
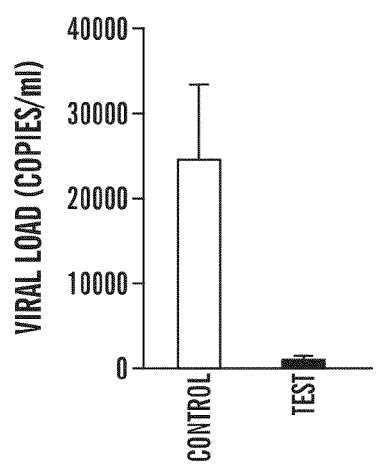

Next the inventors assessed if siRNA treatment could also suppress an established HIV infection. However in the above model, after an exogenous viral challenge, the decline of CD4 T cells to nadir levels occurs extremely fast making it difficult to assess postinfection siRNA treatment efficacy. Thus, as an alternate strategy to mimic an established infection, the inventors reconstituted mice with PBLs from an HIV seropositive donor. This also enabled the inventors to evaluate whether the siRNAs targeting the conserved vif and tat sequences that could protect against the strain of HIV-1 used, as well as whether it was also effective against the multiple viral quasispecies that are likely to be present in infected individuals. PBMC from a donor on HAART treatment for 4 years with viral loads below detection level and a CD4/CD3 ratio of 0.34 (FIG. 3b, input) was used for these experiments. Again, a combination of siRNAs targeting CCR5, vif and tat was used and siRNA administration repeated as indicated in FIG. 3a. As observed with the experimental infection model, in mice reconstituted with HIV infected PBMC and treated with control Luc siRNA, severe CD4+ T cell depletion was observed as early as 10 days after engraftment (mean CD4/CD3 ratios of 0.14) (FIGS. 3b and 3c). In contrast, in the test mice treated with antiviral siRNA, CD4$^+$ T cell levels did not decline, but instead expanded due to xenogenic activation resulting in a steady increase in numbers up to the 2nd week (the percentage of CD4$^+$ T cells increasing to about 60%). In fact, the CD4/CD3 ratios (mean=0.47) remained higher than the input ratios 3.5 weeks after transplantation, suggesting that siRNA treatment has the potential to reverse the CD4 T cell loss in HIV disease. As the viral loads assessed by serum p24 ELISA levels were below detectable levels even in the control mice (probably due to the low numbers of input CD4 T cells), the inventors measured the plasma viral RNA copy numbers. The viral RNA copy numbers were significantly reduced in scFvCD7-9R/antiviral siRNA treated mice compared to control mice (FIG. 3d). Taken together, these results demonstrate that multiplexed siRNAs can serve as effective antiviral treatment analogous to combination antiretroviral therapy in a clinical setting.

Figure 4A:
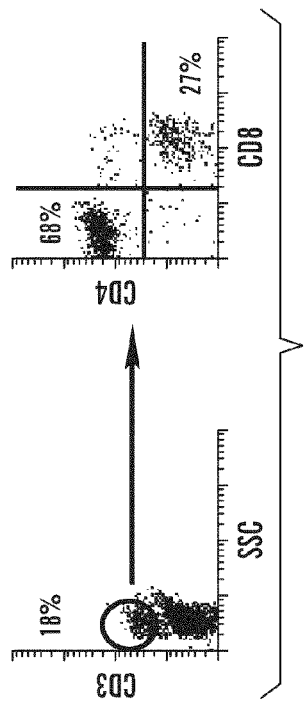
FIGS. 4A-4D shows scFvCD7-9R mediates siRNA delivery to naïve T cells in Hu-HSC mice.
Figure 4B:
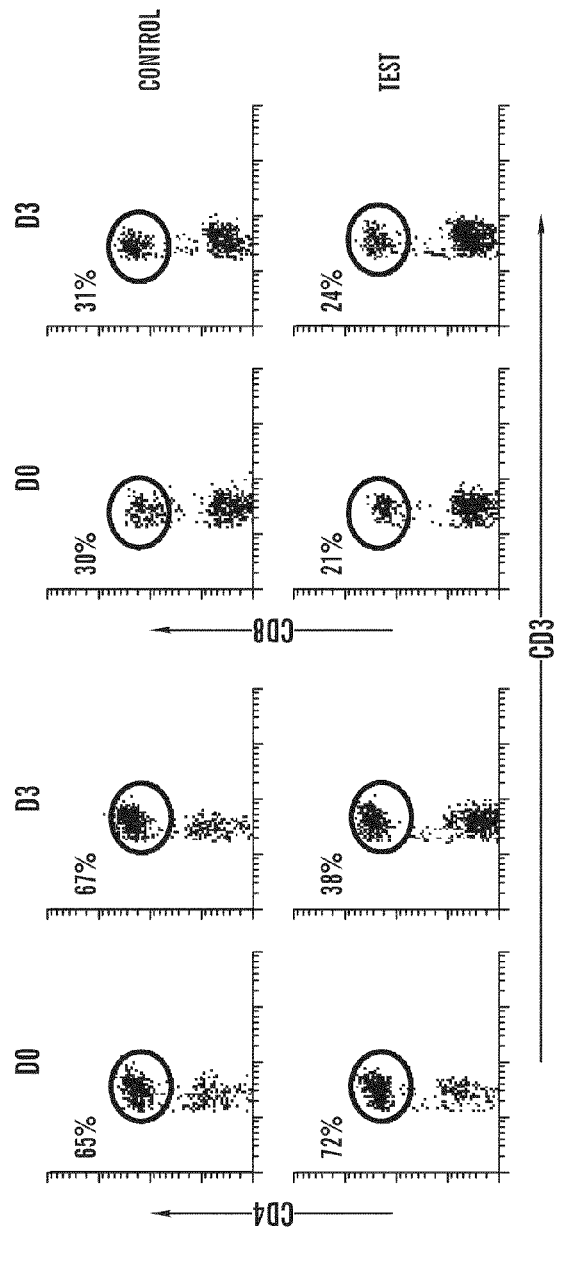
Figure 4C:
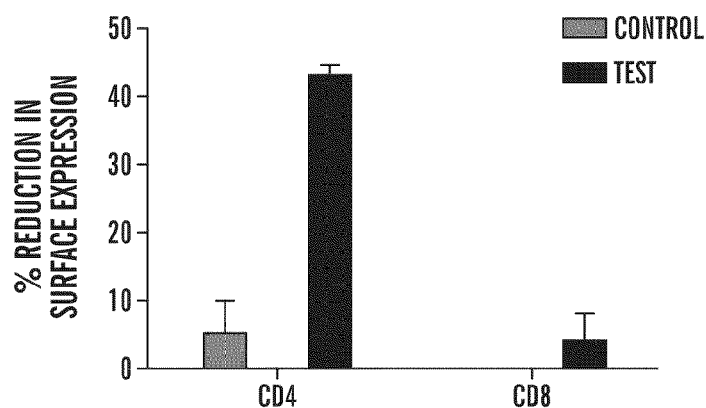
Figure 4D:
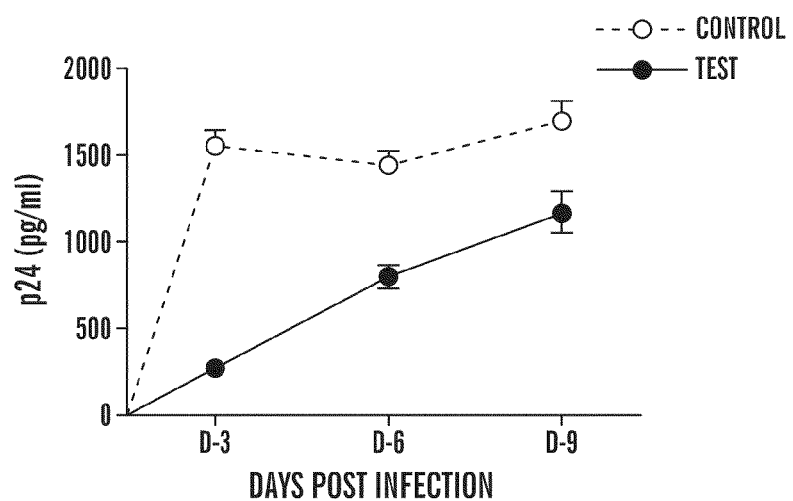
Figure 6B:
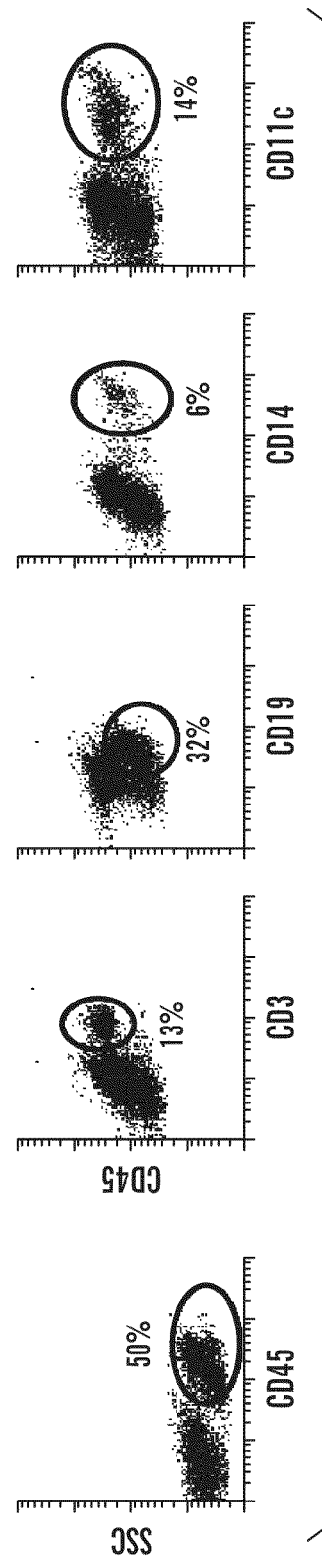
Figure 6C:
Figure 7A:
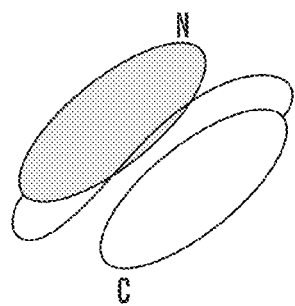
FIGS. 7A-7E show CD7scFv conjugation to 9R enables siRNA binding.
Figure 7B:
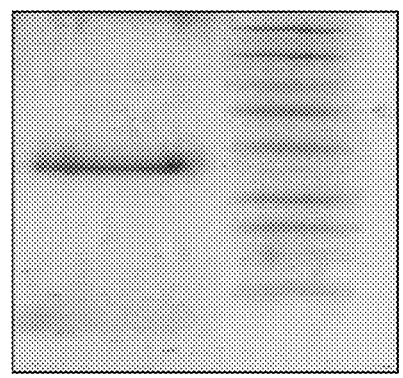
Figure 7C:
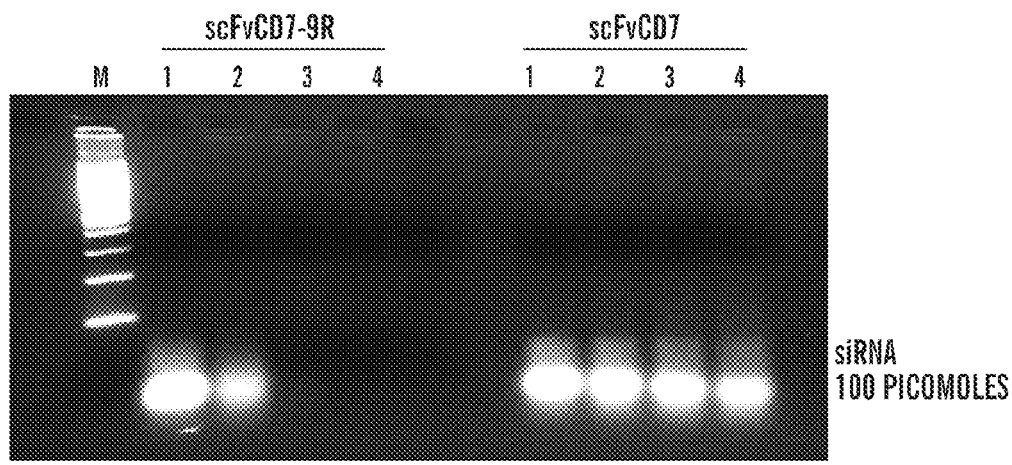
Figure 7D:
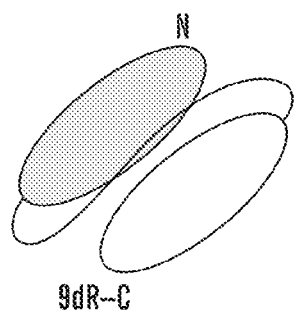
Figure 7E:
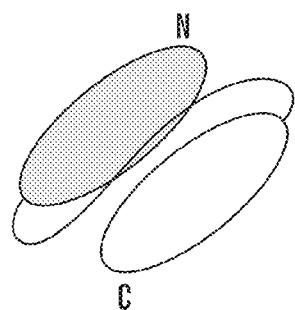
Figure 8B:
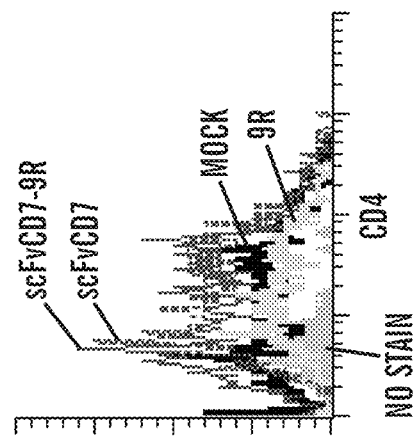
FIGS. 8A-8B show both CD7 scFv and scFv-9dR specifically block CD7 staining in Jurkat cells.
Figure 8A:
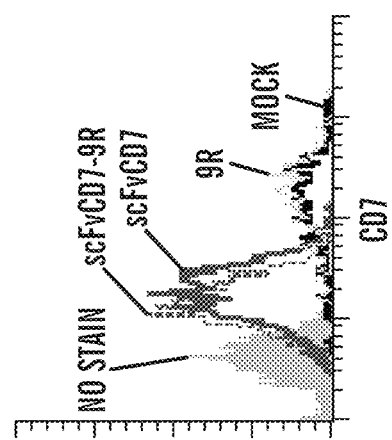
Figure 9A:
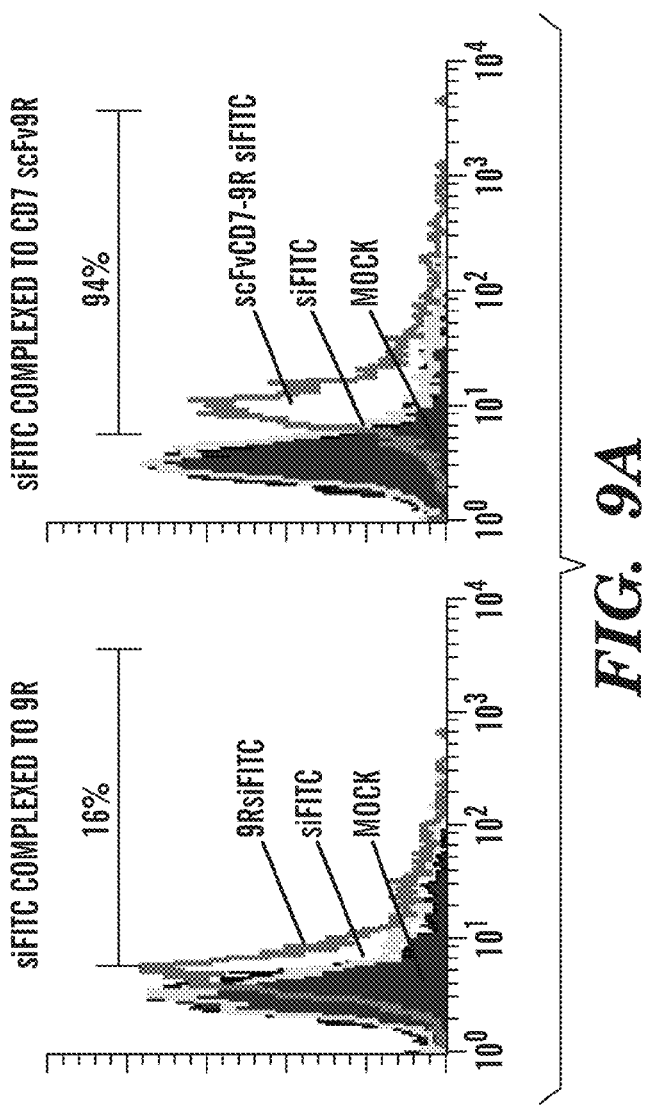
FIGS. 9A-9B show CD7 scFc/9R is able to deliver FITC siRNA to Jurkat cells.
Figure 9B:
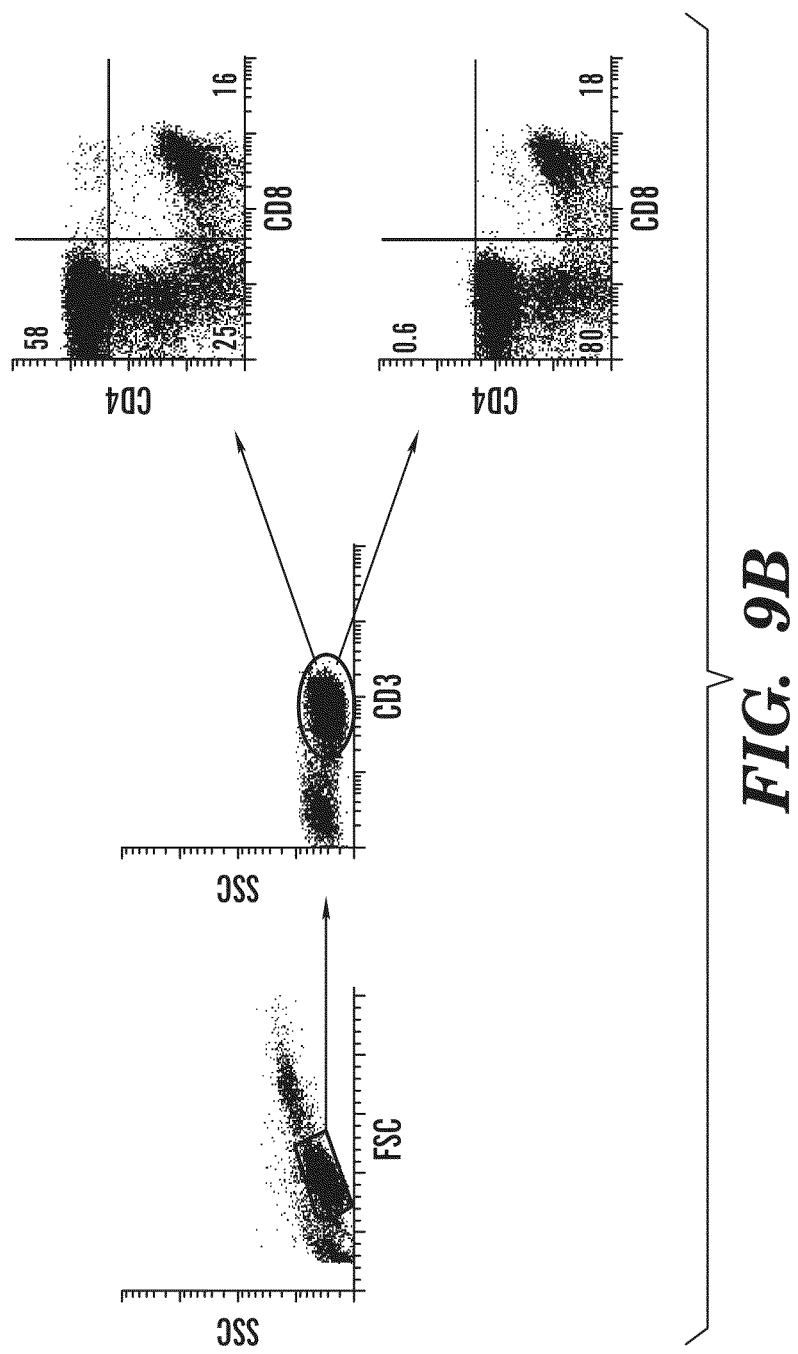
Figure 10A:
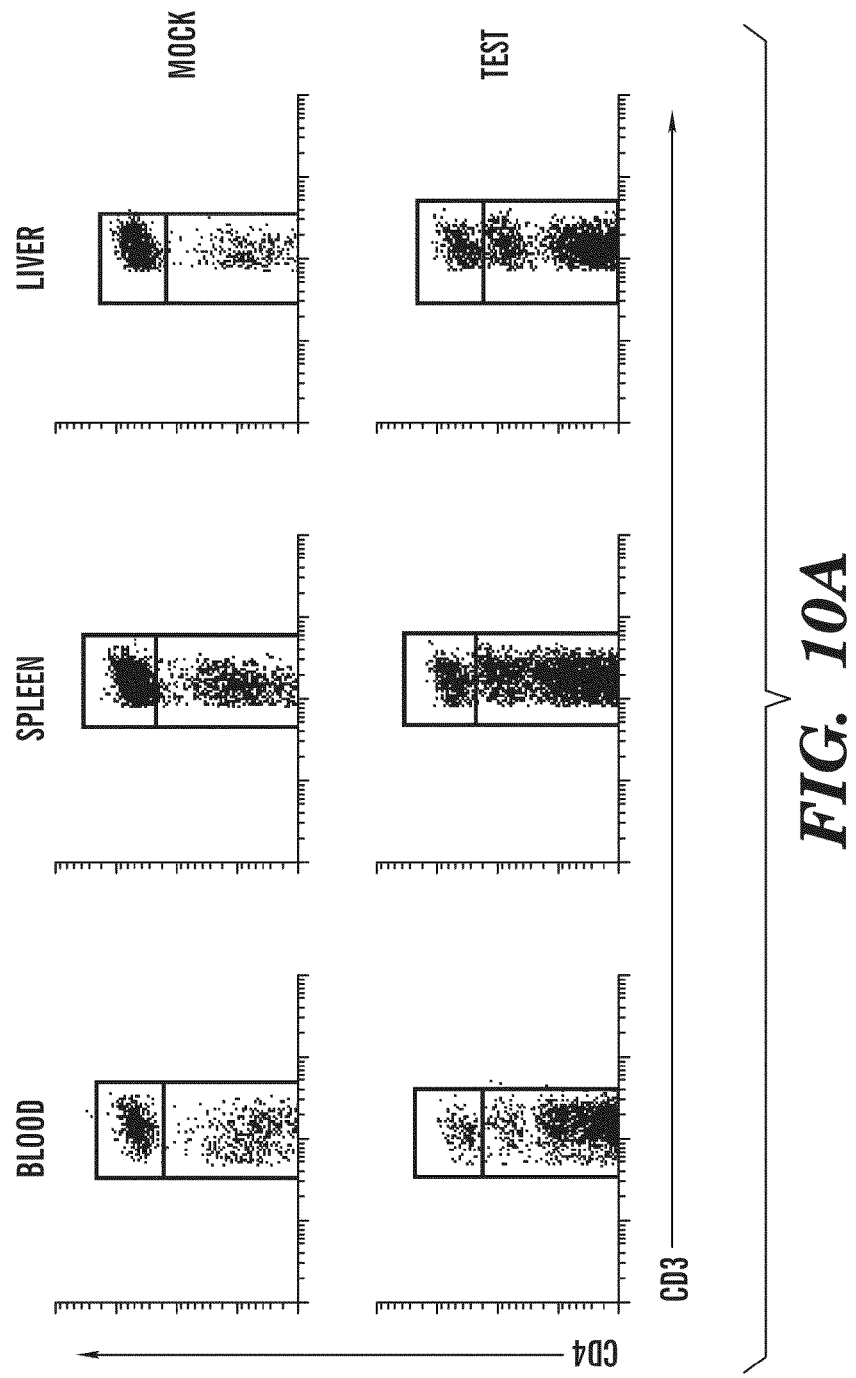
FIGS. 10A-10B show CD4 expression is down-modulated in i.v. injected CD7 scFv/9R-complexed CD4 siRNA in SCID/NOD γc$^{-/-}$ Hu/PBMC mice.
Figure 10B:
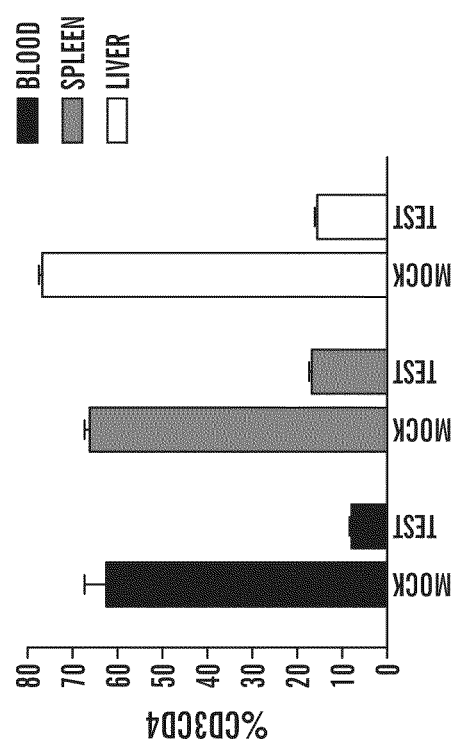
Figure 11A:
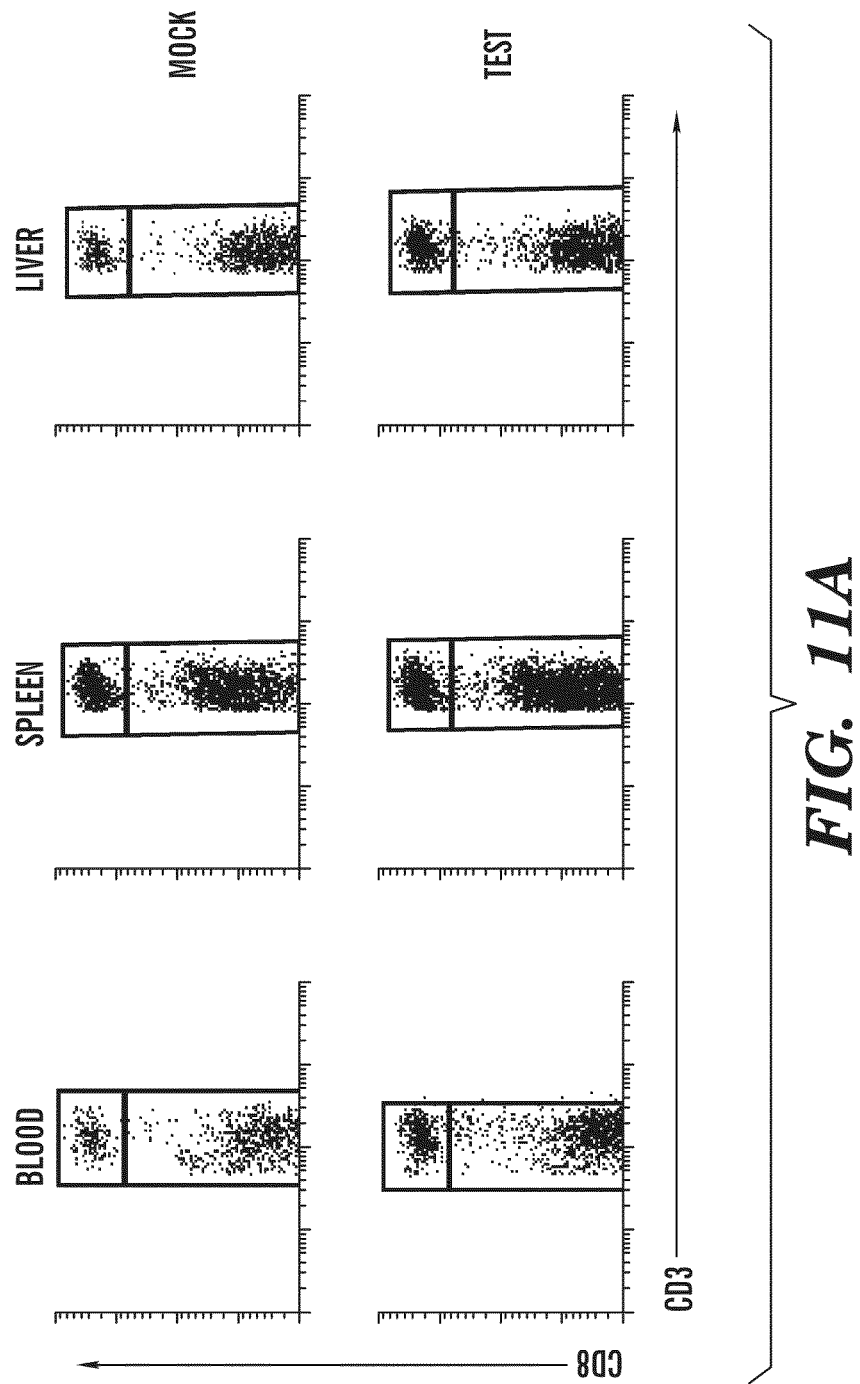
FIG. 11A-11B show CD8 expression is not affected in i.v. injected CD7 scFv/9R-complexed CD4 siRNA in SCID/NOD γc$^{-/-}$ Hu/PBMC mice.
Figure 11B:
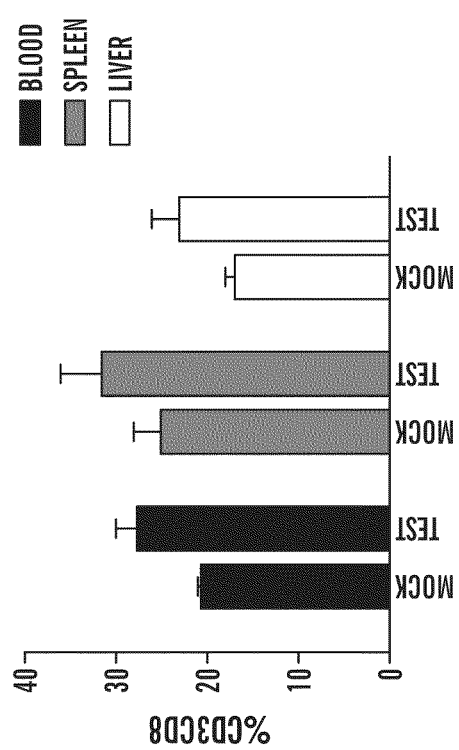

While Hu-PBL mice offer a suitable acute infection model to test antiviral efficacy, because the T cells are activated by xenogenic stimulation, this model precludes testing siRNA delivery to naïve and resting T cells. Thus, the inventors also tested if scFvCD7-9R is able to deliver siRNA to naïve T cells in the Hu-HSC model. In this model, multilineage immune cell reconstitution occurred 12 weeks after HSC transplantation with average levels of 50% human $CD45^+$ lymphocytes in the peripheral blood (FIGS. 6b and 4a). In addition, T cells in these mice exist predominantly as naïve unactivated cells ($CD45RA^{hi}$, $CCR7^{hi}$, $CD62L^{hi}$, $CD27^{hi}$ and $CR5^{lo}$) in contrast to T cells from Hu-PBL mice that display a predominantly activated phenotype (FIG. 6c). To test siRNA delivery, mice were treated with scFvCD7-9R/siCD4 and examined for CD4 gene silencing as described earlier. Remarkably, substantial reduction in CD4 expression was seen in CD3 gated T cells, suggesting that scFvCD7-9R is able to deliver siRNA to naïve T cells (FIGS. 4b and 4c). The inventors also tested the ability of scFvCD7-9R-mediated siRNA delivery to naïve T cells to confer resistance to HIV challenge. Spleen cells harvested from Hu-HSC mice treated 24 hours earlier with a single dose of siCCR5 or control siLuc were stimulated with PHA and infected with $HIV_{BaL}$ (moi=3). The p24 levels in serial culture supernatants were significantly lower in the siCCR5 treated compared to control siLuc treated cell cultures (FIG. 4d). These results are relevant to therapeutic application as resting T cells harboring integrated HIV provirus are an important latent reservoir that can rekindle infection after interruption of $HAART^{22-24}$.

In summary, the inventors have discovered and developed a new approach for systemic siRNA delivery of anti-HIV siRNAs to T cells in a small animal model that closely mirrors human HIV infection. The inventors have demonstrated herein a practical utility, and effective method for siRNA-based therapy for reducing viral load and preventing CD4 T cell loss[8,14,25]. With the treatment approach as disclosed herein, different siRNA combinations can also be changed to keep pace with the mutating virus. The methods and compositions discovered herein by the inventors have a significant advantage over generating shRNA encoding HIV resistant T cells from hematopoietic stem cells, where the siRNA sequence being fixed, the cells will no longer be protected if escape mutants arise. One other issue for treatment of HIV infection is the ability to target macrophages and dendritic cells. In this context, it has been recently reported that an antibody to LFA-1 may be able to target all leukocytes, including macrophages and dendrite cells. Similarly, other peptide- or antibody mediated targeting approaches for macrophage delivery could also be used in combination with scFvCD7-9R. The availability of a preclinical animal model for HIV as disclosed herein also allows for rapid testing of the scFcCD7-9R delivery system to deliver other RNAi agents as well as other therapies as HIV therapies, and related issues such as viral escape and toxicity prior to translating RNAi for clinical use. Because the humanized mouse model essentially replicates the human immune environment in the mouse, the results are expected to be predictive of a similar outcome in human subjects.

REFERENCES

The references cited throughout the specification are herein incorporated by reference in their entirety.

1. Manjunath, N., Kumar, P., Lee, S. K. & Shankar, P. Interfering antiviral immunity: application, subversion, hope? Trends Immunol 27, 328-335 (2006).
2. Scherer, L., Rossi, J. J. & Weinberg, M. S. Progress and prospects: RNA-based therapies for treatment of HIV infection. Gene Ther 14, 1057-1064 (2007).
3. Shankar, P., Manjunath, N. & Lieberman, J. The prospect of silencing disease using RNA interference. Jama 293, 1367-1373 (2005).
4. Dykxhoorn, D. M. & Lieberman, J. Knocking down disease with siRNAs. Cell 126, 231-235 (2006).
5. Lee, S.-K., et al. Lentiviral delivery of short hairpin RNAs protects CD4 T cells from multiple clades and primary isolates of HIV. Blood 106, 818-826 (2005).
6. Novina, C. D., et al. siRNA-directed inhibition of HIV-1 infection. Nat Med 8, 681-686 (2002).
7. Song, E., et al. Sustained Small Interfering RNA-Mediated Human Immunodeficiency Virus Type 1 Inhibition in Primary Macrophages. J. Virol. 77, 7174-7181 (2003).
8. Song, E., et al. Antibody mediated in vivo delivery of small interfering RNAs via cell-surface receptors. Nat Biotech 23, 709-717 (2005).
9. ter Brake, O., Konstantinova, P., Ceylan, M. & Berkhout, B. Silencing of HIV-1 with RNA interference: a multiple shRNA approach. Mol Ther 14, 883-892 (2006).
10. Ishikawa, F., et al. Development of functional human blood and immune systems in NOD/SCID/IL2 receptor {gamma} chain null mice. Blood 106, 1565-1573 (2005).
11. Baenziger, S., et al. Disseminated and sustained HIV infection in CD34+ cord blood cell-transplanted Rag2−/− {gamma}c−/− mice. Proceedings of the National Academy of Sciences 103, 15951-15956 (2006).
12. Traggiai, E., et al. Development of a Human Adaptive Immune System in Cord Blood Cell-Transplanted Mice. Science 304, 104-107 (2004).
13. Shultz, L. D., Ishikawa, F. & Greiner, D. L. Humanized mice in translational biomedical research. Nat Rev Immunol 7, 118-130 (2007).
14. Kumar, P., et al. Transvascular delivery of small interfering RNA to the central nervous system. Nature 448, 39-43 (2007).
15. Bremer, E., et al. Target Cell-Restricted Apoptosis Induction of Acute Leukemic T Cells by a Recombinant Tumor Necrosis Factor-Related Apoptosis-Inducing Ligand Fusion Protein with Specificity for Human CD7. Cancer Res 65, 3380-3388 (2005).
16. Frankel, A. E., et al. Therapy of patients with T-cell lymphomas and leukemias using an anti-CD7 monoclonal antibody-ricin A chain immunotoxin. Leuk Lymphoma 26, 287-298 (1997).
17. Peipp, M., et al. A Recombinant CD7-specific Single-Chain Immunotoxin Is a Potent Inducer of Apoptosis in Acute Leukemic T Cells. Cancer Res 62, 2848-2855 (2002).
18. Nakata, H., et al. Potent Anti-R5 Human Immunodeficiency Virus Type 1 Effects of a CCR5 Antagonist, AK602/ONO4128/GW873140, in a Novel Human Peripheral Blood Mononuclear Cell Nonobese Diabetic-SCID, Interleukin-2 Receptor {gamma}-Chain-Knocked-Out AIDS Mouse Model. J. Virol. 79, 2087-2096 (2005).
19. Fais, S., et al. Human Immunodeficiency Virus Type 1 Strains R5 and X4 Induce Different Pathogenic Effects in hu-PBL-SCID Mice, Depending on the State of Activation/Differentiation of Human Target Cells at the Time of Primary Infection. J. Virol. 73, 6453-6459 (1999).
20. Berges, B., Wheat, W., Palmer, B., Connick, E. & Akkina, R. HIV-1 infection and CD4 T cell depletion in the humanized Rag2-/-gamma c-/- (RAG-hu) mouse model. Retrovirology 3, 76 (2006).
21. von Eije, K. J., ter Brake, O. & Berkhout, B. HIV-1 escape is restricted when conserved genome sequences are targeted by RNA interference. J. Virol., JVI.02035-02007 (2007).
22. Chun, T.-W., et al. Presence of an inducible HIV-1 latent reservoir during highly active antiretroviral therapy. Proceedings of the National Academy of Sciences 94, 13193-13197 (1997).
23. Finzi, D., et al. Latent infection of CD4+ T cells provides a mechanism for lifelong persistence of HIV-1, even in patients on effective combination therapy. Nat Med 5, 512-517 (1999).
24. Brooks, D. G., Kitchen, S. G., Kitchen, C. M., Scripture-Adams, D. D. & Zack, J. A. Generation of HIV latency during thymopoiesis. Nat Med 7, 459-464 (2001).
25. Peer, D., Zhu, P., Carman, C. V., Lieberman, J. & Shimaoka, M. Selective gene silencing in activated leukocytes by targeting siRNAs to the integrin lymphocyte function-associated antigen-1. Proc Natl Acad Sci USA 104, 4095-4100 (2007).
26. Surabhi, R. M. & Gaynor, R. B. RNA interference directed against viral and cellular targets inhibits human immunodeficiency Virus Type 1 replication. J Virol 76, 12963-12973 (2002).
27. Wan, L., et al. Expression, purification, and refolding of a novel immunotoxin containing humanized single-chain fragment variable antibody against CTLA4 and the N-terminal fragment of human perforin. Protein Expression and Purification 48, 307-313 (2006).
28. Zeng, F., et al. A protocol for PAIR: PNA-assisted identification of RNA binding proteins in living cells. Nat. Protocols 1, 920-927 (2006).
29. Mosier, D. E., et al. Human immunodeficiency virus infection of human-PBL-SCID mice. Science 251, 791-794 (1991).
30. King, M., et al. A new Hu-PBL model for the study of human islet alloreactivity based on NOD-scid mice bearing a targeted mutation in the IL-2 receptor gamma chain gene. Clinical Immunology In Press, Corrected Proof.

We claim:

1. A composition comprising a targeting moiety associated with a binding moiety, wherein a double stranded RNA segment is associated with the binding moiety, wherein the targeting moiety is an antibody or antigen binding fragment thereof which binds to CD7, and the binding moiety is an oligo-9-peptide (9R), wherein the oligo-9-peptide comprises 9 consecutive arginines.

2. The composition of claim 1, wherein the targeting moiety specifically binds to a cell-surface antigen on a target cell, wherein the cell surface antigen internalizes when the targeting moiety binds the cell surface antigen.

3. The composition of claim 2, wherein the target cell is a T-cell.

4. The composition of claim 1, wherein the targeting moiety and binding moiety are comprised as a fusion protein, wherein the binding moiety is fused to the carboxy portion of the targeting moiety.

5. The composition of claim 2, wherein the cell is selected from the group consisting of a cultured cell, cell that is part of an organ, a cell that is part of a subject and an embryonic stem cell.

6. The composition of claim 5, wherein the subject is a human.

* * * * *